United States Patent
Niimi et al.

(10) Patent No.: US 11,374,044 B2
(45) Date of Patent: Jun. 28, 2022

(54) MATERIAL FOR PHOTOELECTRIC CONVERSION ELEMENT FOR USE IN IMAGING ELEMENT, AND PHOTOELECTRIC CONVERSION ELEMENT INCLUDING SAME

(71) Applicant: Nippon Kayaku Kabushiki Kaisha, Tokyo (JP)

(72) Inventors: Kazuki Niimi, Tokyo (JP); Yusuke Tone, Tokyo (JP); Hidenori Yakushiji, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 819 days.

(21) Appl. No.: 16/318,240

(22) PCT Filed: Jul. 18, 2017

(86) PCT No.: PCT/JP2017/025882
§ 371 (c)(1),
(2) Date: Jan. 16, 2019

(87) PCT Pub. No.: WO2018/016465
PCT Pub. Date: Jan. 25, 2018

(65) Prior Publication Data
US 2019/0157321 A1    May 23, 2019

(30) Foreign Application Priority Data

Jul. 19, 2016 (JP) ............................ JP2016-141373
Aug. 29, 2016 (JP) ................................ 2016-166546
Dec. 7, 2016 (JP) ................................ 2016-237629
May 24, 2017 (JP) ................................ 2017-102724

(51) Int. Cl.
| | |
|---|---|
| C07D 495/04 | (2006.01) |
| C07D 277/66 | (2006.01) |
| C07D 307/79 | (2006.01) |
| C07D 307/87 | (2006.01) |
| C07D 333/54 | (2006.01) |
| C07D 333/72 | (2006.01) |
| H01L 27/146 | (2006.01) |
| H01L 51/00 | (2006.01) |
| H01L 31/10 | (2006.01) |
| H01L 51/42 | (2006.01) |
| H01L 27/30 | (2006.01) |
| H01L 29/786 | (2006.01) |
| H01L 51/44 | (2006.01) |

(52) U.S. Cl.
CPC ........ *H01L 27/1462* (2013.01); *C07D 495/04* (2013.01); *H01L 27/14643* (2013.01); *H01L 27/301* (2013.01); *H01L 29/78603* (2013.01); *H01L 31/10* (2013.01); *H01L 51/0071* (2013.01); *H01L 51/0073* (2013.01); *H01L 51/0074* (2013.01); *H01L 51/424* (2013.01); *H01L 51/441* (2013.01); *H01L 27/307* (2013.01); *H01L 51/4213* (2013.01); *Y02E 10/549* (2013.01)

(58) Field of Classification Search
CPC .. C07D 495/04; C07D 277/66; C07D 307/79; C07D 307/87; C07D 333/54; C07D 333/72; H01L 27/1462; H01L 51/441; H01L 27/301; H01L 27/14643; H01L 51/4213; H01L 51/0071; H01L 51/0073; H01L 51/0074
USPC ...................... 549/42, 49, 462; 548/159, 156
See application file for complete search history.

(56) References Cited

U.S. PATENT DOCUMENTS

| | | | |
|---|---|---|---|
| 2006/0278869 A1 | 12/2006 | Hioki et al. | |
| 2008/0142792 A1 | 6/2008 | Park et al. | |
| 2010/0032655 A1 | 2/2010 | Takimiya et al. | |
| 2011/0303910 A1 | 12/2011 | Kuwabara et al. | |
| 2017/0040550 A1 | 2/2017 | Yakushiji et al. | |

FOREIGN PATENT DOCUMENTS

| | | |
|---|---|---|
| JP | 2008258592 A | 10/2008 |
| JP | 2008290963 A | 12/2008 |
| JP | 2009246140 A | 10/2009 |
| JP | 4945146 B2 | 6/2012 |
| JP | 5022573 B2 | 6/2012 |
| WO | 2008047896 A1 | 4/2008 |
| WO | 2010098372 A1 | 2/2010 |

(Continued)

OTHER PUBLICATIONS

Takimiya et al., "2, 7-Diphenyl[1]benzothieno[3,2-b]benzothiophene, A New Organic Semiconductor for Air-Stable Organiz Field-Effect Transistors with Mobilities up to 2.0 cm2V-1s-1"; Journal of the American Chemical Society, 2006, pp. 12604-12605, vol. 128, No. 39.

(Continued)

*Primary Examiner* — Joseph R Kosack
*Assistant Examiner* — Sagar Patel
(74) *Attorney, Agent, or Firm* — The Webb Law Firm

(57) ABSTRACT

The present invention pertains to a material for a photoelectric conversion element for use in an imaging element, the material containing a compound represented by formula (1) (in formula (1), $R_1$ and $R_2$ independently represent a substituted or unsubstituted fused heterocyclic aromatic group). The material can provide a photoelectric conversion element having excellent hole and electron leakage preventing properties, hole and electron transport properties, heat tolerance to processing temperatures, and visible light transparency.

16 Claims, 1 Drawing Sheet

(56) References Cited

FOREIGN PATENT DOCUMENTS

WO    2015163349 A1    10/2015

OTHER PUBLICATIONS

Izawa et al., "Molecular Modification of 2,7-Diphenyl[1]benzothieno[3,2-b]benzothiophene (DPh-BTBT) with Diarylamino Substituents: From Crystaline Order to Amorphous State in Evaporated Thin Films", Chemistry Letters, 2009, pp. 420-421, vol. 38, No. 5.

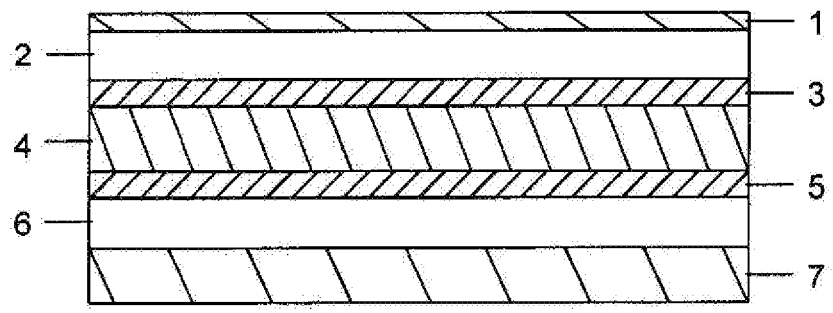

MATERIAL FOR PHOTOELECTRIC CONVERSION ELEMENT FOR USE IN IMAGING ELEMENT, AND PHOTOELECTRIC CONVERSION ELEMENT INCLUDING SAME

CROSS-REFERENCE TO RELATED APPLICATIONS

This application is the United States national phase of International Application No. PCT/JP2017/025882 filed Jul. 18, 2017, and claims priority to Japanese Patent Application Nos. 2016-141373 filed Jul. 19, 2016, 2016-166546 filed Aug. 29, 2016, 2016-237629 filed Dec. 7, 2016, and 2017-102724 filed May 24, 2017, the disclosures of which are hereby incorporated in their entirety by reference.

TECHNICAL FIELD

The present invention relates to a novel fused polycyclic aromatic compound that may be used for photoelectric conversion elements, imaging elements, photosensors, organic semiconductor devices, and the like.

BACKGROUND ART

In recent years, organic electronic devices have received growing attention. Examples of their features include flexibility, possible large areas, and inexpensive and high-speed printing methods available in electronic device manufacturing processes. Typical examples of the organic electronic devices include organic EL elements, organic solar cell elements, organic photoelectric conversion elements, and organic transistor elements. Flat panel displays including the organic EL elements are expected as main targets for next-generation display purposes and applied to mobile phone displays, TV, etc. The flat panel displays are still under development with the aim of higher functionalization. Organic solar cell elements, etc., are used as flexible and inexpensive energy sources, and research and development are ongoing as to flexible displays or inexpensive ICs including the organic transistor elements, etc.

For the development of the organic electronic devices, it is very important to develop materials constituting the devices. A large number of materials have thus been studied in each field. Nonetheless, conventional materials do not have sufficient performance, and materials useful for various devices are still being developed energetically. Among others, compounds having a benzothienobenzothiophene backbone and the like have been developed as organic electronic materials (Patent Literatures 1 to 3). Alkyl derivatives of benzothienobenzothiophene have sufficient solubility in solvents to form semiconductor thin films in the printing processes. However, such derivatives are apt to undergo a phase transition at low temperatures because the number of fused rings relative to the alkyl chain length is small, and there has been the problem that the thermal resistance of the organic electronic devices is poor.

Meanwhile, among recent organic electronic elements, the organic photoelectric conversion elements are expected to be expanded to next-generation imaging elements, and some groups have made reports thereon. Examples thereof include use of a quinacridone derivative or a quinazoline derivative in a photoelectric conversion element (Patent Literature 4), application of a photoelectric conversion element using a quinacridone derivative to an imaging element (Patent Literature 5), and use of a diketopyrrolopyrrole derivative (Patent Literature 6). In general, it is considered that the performance of imaging elements is improved by reduction in dark current for the purpose of high contrasts and electric power saving. Thus, an approach of inserting a hole blocking layer or an electron blocking layer between a photoelectric conversion portion and an electrode portion is used for decreasing leakage current from the photoelectric conversion portion in the dark.

The hole blocking layer and the electron blocking layer are generally used widely in the field of organic electronic devices. In a laminated film constituting a device, each of the hole blocking layer and the electron blocking layer is disposed at the interface between an electrode or a conductive film and the other films, and has the function of controlling the back transfer of holes or electrons. The hole blocking layer and the electron blocking layer adjust the leakage of unnecessary holes or electrons and are selected for use in consideration of characteristics such as thermal resistance, transmitted wavelengths, and film formation methods depending on the purpose of the device. However, the required performance of materials for photoelectric conversion element purposes is particularly high, and conventional hole blocking layers or electron blocking layers do not have sufficient performance in terms of leakage current prevention properties, thermal resistance to processing temperatures, transparency to visible light, etc., and are in short of commercial exploitation.

CITATION LIST

Patent Literature

Patent Literature 1: Japanese Patent Laid-Open No. 2008-258592
Patent Literature 2: International Publication No. WO 2008/047896
Patent Literature 3: International Publication No. WO 2010/098372
Patent Literature 4: Japanese Patent No. 4945146
Patent Literature 5: Japanese Patent No. 5022573
Patent Literature 6: Japanese Patent Laid-Open No. 2008-290963

Non Patent Literature

Non Patent Literature 1: J. Am. Chem. Soc., 2006, 128 (39), 12604

SUMMARY OF INVENTION

Technical Problem

The present invention has been made in light of these circumstances, and an object of the present invention is to provide a fused polycyclic aromatic compound as a material that may be used for various electronic devices including a photoelectric conversion element which is excellent in hole- or electron-leak prevention properties, hole or electron transport properties, thermal resistance to processing temperatures, transparency to visible light, etc., and an organic transistor which is excellent in mobility and thermal resistance.

Solution to Problem

The present inventors have conducted diligent studies to attain the object described above and consequently completed the present invention by finding that the object is attained by using a compound represented by the formula (1) given below. Specifically, the present invention is as follows:

[1] a material for a photoelectric conversion element for use in an imaging element, comprising a compound represented by the following formula (1):

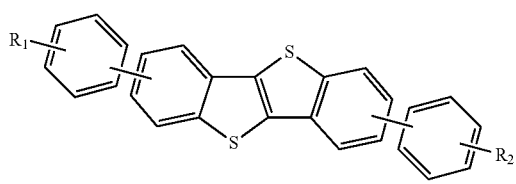
(1)

wherein $R_1$ and $R_2$ independently represent a substituted or unsubstituted fused heterocyclic aromatic group;

[2] the material for a photoelectric conversion element for use in an imaging element according to [1], wherein the compound of the formula (1) is a compound represented by the following formula (2):

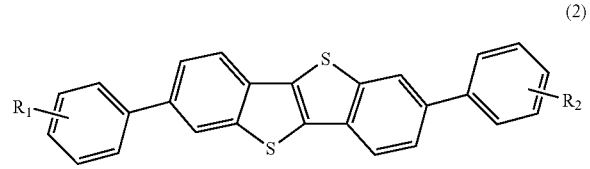
(2)

wherein $R_1$ and $R_2$ are the same as $R_1$ and $R_2$ defined in the formula (1) according to [1];

[3] the material for a photoelectric conversion element for use in an imaging element according to [2], wherein the compound of the formula (2) is a compound represented by the following formula (3):

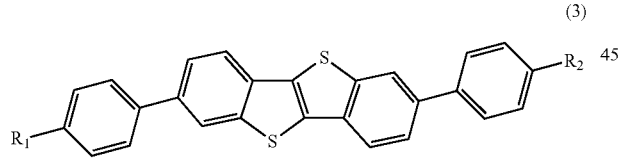
(3)

wherein $R_1$ and $R_2$ are the same as $R_1$ and $R_2$ defined in the formula (1) according to [1];

[4] the material for a photoelectric conversion element for use in an imaging element according to any one of [1] to [3], wherein $R_1$ and $R_2$ each represent a fused heterocyclic aromatic group containing a sulfur atom or an oxygen atom;

[5] the material for a photoelectric conversion element for use in an imaging element according to [4], wherein $R_1$ and $R_2$ each represent a substituted or unsubstituted aromatic group condensed with furan, a substituted or unsubstituted aromatic group condensed with thiophene, or a substituted or unsubstituted aromatic group condensed with thiazole;

[6] the material for a photoelectric conversion element for use in an imaging element according to [5], wherein $R_1$ and $R_2$ each represent substituted or unsubstituted benzo[b]furan, substituted or unsubstituted benzo[b]thiophene, or substituted or unsubstituted 2-benzo[d]thiazole group;

[7] a photoelectric conversion element for use in an imaging element, comprising the material for a photoelectric conversion element for use in an imaging element according to any one of [1] to [6];

[8] a photoelectric conversion element for use in an imaging element, comprising a p-type organic semiconductor material and an n-type organic semiconductor material wherein the p-type organic semiconductor material comprises the material for a photoelectric conversion element for use in an imaging element according to any one of [1] to [6];

[9] a photoelectric conversion element for use in an imaging element, comprising a first electrode film (A), a second electrode film (B), and a photoelectric conversion portion (C) disposed between the first electrode film and the second electrode film, wherein the photoelectric conversion portion (C) comprises at least a photoelectric conversion layer (c-1) and an organic thin-film layer (c-2) other than the photoelectric conversion layer, and wherein the organic thin-film layer (c-2) other than the photoelectric conversion layer comprises the material for a photoelectric conversion element for use in an imaging element according to any one of [1] to [6];

[10] the photoelectric conversion element for use in an imaging element according to [9], wherein the organic thin-film layer (c-2) other than the photoelectric conversion layer is an electron blocking layer;

[11] the photoelectric conversion element for use in an imaging element according to [9], wherein the organic thin-film layer (c-2) other than the photoelectric conversion layer is a hole blocking layer;

[12] the photoelectric conversion element for use in an imaging element according to [9], wherein the organic thin-film layer (c-2) other than the photoelectric conversion layer is an electron transport layer;

[13] the photoelectric conversion element for use in an imaging element according to [9], wherein the organic thin-film layer (c-2) other than the photoelectric conversion layer is a hole transport layer;

[14] the photoelectric conversion element for use in an imaging element according to any one of [7] to [13], further comprising a thin-film transistor (D) comprising a hole accumulation portion and a signal readout portion (E) that reads a signal responding to charge accumulated in the thin-film transistor;

[15] the photoelectric conversion element for use in an imaging element according to [14], wherein the thin-film transistor (D) comprising a hole accumulation portion further comprises a connection portion (d) electrically connecting the hole accumulation portion to any one of the first electrode film and the second electrode film;

[16] an imaging element comprising a plurality of photoelectric conversion elements for use in an imaging element according to any one of [7] to [15] arranged in an array; and

[17] a photosensor comprising the photoelectric conversion element for use in an imaging element according to any one of [7] to [15] or the imaging element according to [16].

Advantageous Effects of the Invention

The present invention can provide a novel photoelectric conversion element for use in an imaging element which comprises a compound represented by the formula (1) and is excellent in required characteristics such as hole- or electron-leakage prevention, hole or electron transport properties, thermal resistance, and transparency to visible light.

BRIEF DESCRIPTION OF DRAWINGS

FIG. 1 shows a cross-sectional view illustrating an embodiment of the photoelectric conversion element for use in an imaging element of the present invention.

DESCRIPTION OF EMBODIMENT

The contents of the present invention will be described in detail. The explanation about configuration requirements described below is based on typical embodiments and specific examples of the present invention. However, the present invention is not intended to be limited by such embodiments or specific examples.

A feature of a material for a photoelectric conversion element for use in an imaging element of the present invention is that the material contains a compound represented by the following general formula (1):

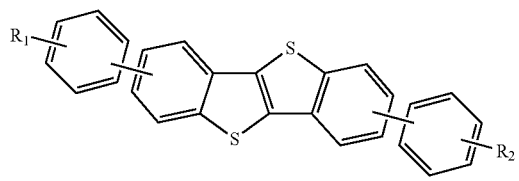

(1)

In the formula (1) described above, $R_1$ and $R_2$ independently represent a substituted or unsubstituted fused heterocyclic aromatic group.

The fused heterocyclic aromatic group represented by each of $R_1$ and $R_2$ in the formula (1) means a residue formed by removing one hydrogen atom from a fused heterocyclic aromatic compound. Specific examples of such a group include a benzothienyl group, a naphthothienyl group, an anthrathienyl group, a benzodithienyl group, a dibenzothienyl group, a benzotrithienyl group, a thienothienyl group, a benzofuranyl group, a naphthofuranyl group, an anthrafuranyl group, a benzodifuranyl group, a dibenzofuranyl group, a benzotrifuranyl group, a benzothiazole group, a naphthothiazole group, an anthrathiazole group, a benzodithiazole group, a benzotrithiazole group, a quinolyl group, an isoquinolyl group, a benzopyrrolyl group, an indolenyl group, a benzoimidazolyl group, a carbazolyl group, a xanthenyl group, and a thioxanthenyl group. Among these, a fused heterocyclic aromatic group that contains a thiophene ring, a furan ring, or a thiazole ring as the hetero ring is preferable, a benzothienyl group, a benzofuranyl group, or a benzothiazole group is more preferable, a 2-benzo[b]thienyl group, a 2-benzo[b]furanyl group, or a 2-benzo[d]thiazole group is further preferable, and a 2-benzo[d]thiazole group is particularly preferable. $R_1$ and $R_2$ may be either the same or different, preferably the same.

In this context, the "substituted or unsubstituted fused heterocyclic aromatic group" means a fused heterocyclic aromatic group in which hydrogen atom(s) of the fused heterocyclic aromatic group is substituted by substituent(s) or a fused heterocyclic aromatic group in which hydrogen atom(s) of the fused heterocyclic aromatic group is not substituted by substituent(s). When the fused heterocyclic aromatic group has substituent(s), the aromatic group may have at least one substituent, and the position(s) of substitution and the number of substituents are not particularly limited.

Examples of the substituent on the fused heterocyclic aromatic group represented by each of $R_1$ and $R_2$ in the formula (1) include, but are not limited to, an alkyl group, an alkoxy group, an aromatic group, a halogen atom, a hydroxy group, a mercapto group, a nitro group, an alkyl-substituted amino group, an aryl-substituted amino group, an unsubstituted amino group ($NH_2$ group), an acyl group, an alkoxycarbonyl group, a cyano group, and an isocyano group.

The alkyl group as the substituent on the fused heterocyclic aromatic group represented by each of $R_1$ and $R_2$ in the formula (1) is not limited to linear, branched, or cyclic. Specific examples of the alkyl group as the substituent on the fused heterocyclic aromatic group represented by each of $R_1$ and $R_2$ include linear or branched alkyl groups each having 1 to 36 carbon atoms, such as a methyl group, an ethyl group, a propyl group, an isopropyl group, a n-butyl group, an isobutyl group, a t-butyl group, a n-pentyl group, an isopentyl group, a t-pentyl group, a sec-pentyl group, a n-hexyl group, an isohexyl group, a n-heptyl group, a sec-heptyl group, a n-octyl group, a n-nonyl group, a sec-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a docosyl group, a n-pentacosyl group, a n-octacosyl group, a n-tricontyl group, a 5-(n-pentyl)decyl group, a heneicosyl group, a tricosyl group, a tetracosyl group, a hexacosyl group, a heptacosyl group, a nonacosyl group, a n-triacontyl group, a squaryl group, a dotriacontyl group, and hexatriacontyl group. The alkyl group is preferably a linear or branched alkyl group having 1 to 24 carbon atoms, more preferably a linear or branched alkyl group having 1 to 20 carbon atoms, further preferably a linear or branched alkyl group having 1 to 12 carbon atoms, particularly preferably a linear or branched alkyl group having 1 to 6 carbon atoms, most preferably a linear or branched alkyl group having 1 to 4 carbon atoms. Among these, a linear or branched alkyl group having one or two carbon atoms is preferable. The cycloalkyl group is preferably a cycloalkyl group having 5 to 10 carbon atoms, such as a cyclopentyl group and a cyclohexyl group, more preferably a cycloalkyl group having 5 or 6 carbon atoms.

Specific examples of the alkoxy group as the substituent on the fused heterocyclic aromatic group represented by each of $R_1$ and $R_2$ in the formula (1) include alkoxy groups each having 1 to 36 carbon atoms, such as a methoxy group, an ethoxy group, a propoxy group, an isopropoxy group, a n-butoxy group, an isobutoxy group, a t-butoxy group, a n-pentyloxy group, an isopentyloxy group, a t-pentyloxy group, a sec-pentyloxy group, a n-hexyloxy group, an isohexyloxy group, a n-heptyloxy group, a sec-heptyloxy group, a n-octyloxy group, a n-nonyloxy group, a sec-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, a n-eicosyloxy group, a docosyloxy group, a n-pentacosyloxy group, a n-octacosyloxy group, a n-tricontyloxy group, a 5-(n-pentyl)decyloxy group, a heneicosyloxy group, a tricosyloxy group, a tetracosyloxy group, a hexacosyloxy group, a heptacosyloxy group, a nonacosyloxy group, a n-triacontyloxy group, a squaryloxy group, a dotriacontyloxy group, and a hexatriacontyloxy group. The alkoxy group is preferably an alkoxy group having 1 to 24 carbon atoms, more preferably an alkoxy group having 1 to 20 carbon atoms, further preferably an alkoxy group having 1 to 12 carbon atoms, particularly preferably an alkoxy group having 1 to 6 carbon atoms, most preferably an alkoxy group having 1 to 4 carbon atoms.

Specific examples of the aromatic group as the substituent on the fused heterocyclic aromatic group represented by each of $R_1$ and $R_2$ in the formula (1) include not only aromatic hydrocarbon groups such as a phenyl group and a naphthyl group but also the fused heterocyclic aromatic groups described above. Aromatic hydrocarbon groups are preferable. The aromatic group as the substituent on the fused heterocyclic aromatic group may carry a substituent such as the same substituent as the substituent on the fused heterocyclic aromatic group represented by each of the $R_1$ and $R_2$ in the formula (1).

Specific examples of the halogen atom as the substituent on the fused heterocyclic aromatic group represented by each of $R_1$ and $R_2$ in the formula (1) include a fluorine atom, a chlorine atom, a bromine atom, and an iodine atom.

The alkyl-substituted amino group as the substituent on the fused heterocyclic aromatic group represented by each of $R_1$ and $R_2$ in the formula (1) is not limited to any of monoalkyl-substituted amino groups and dialkyl-substituted amino groups. Examples of the alkyl group for these alkyl-substituted amino groups include the same as those listed as the alkyl group as the substituent on the fused heterocyclic aromatic group represented by each of $R_1$ and $R_2$ in the formula (1).

The aryl-substituted amino group as the substituent on the fused heterocyclic aromatic group represented by each of $R_1$ and $R_2$ in the formula (1) is not limited to any of monoaryl-substituted amino groups and diaryl-substituted amino groups. Examples of the aryl group for these aryl-substituted amino groups include the same as the aromatic hydrocarbon groups described as the substituent on the fused heterocyclic aromatic group represented by each of $R_1$ and $R_2$ in the formula (1).

Examples of the acyl group as the substituent on the fused heterocyclic aromatic group represented by each of $R_1$ and $R_2$ in the formula (1) include substituents composed of a carbonyl group (=CO group) bonded to the aromatic hydrocarbon group described as the substituent on the fused heterocyclic aromatic group represented by each of $R_1$ and $R_2$ in the formula (1) or the alkyl group described as the substituent on the fused heterocyclic aromatic group represented by each of $R_1$ and $R_2$ in the formula (1).

Examples of the alkoxycarbonyl group as the substituent on the fused heterocyclic aromatic group represented by each of $R_1$ and $R_2$ in the formula (1) include substituents composed of a carbonyl group bonded to the alkoxy group as the substituent on the fused heterocyclic aromatic group represented by each of $R_1$ and $R_2$ in the formula (1).

The substituent on the fused heterocyclic aromatic group represented by each of $R_1$ and $R_2$ in the formula (1) is preferably an alkyl group, an aromatic group, a halogen atom, or an alkoxyl group, more preferably a halogen atom or an unsubstituted aromatic hydrocarbon group, further preferably a phenyl group or a biphenyl group.

Both of $R_1$ and $R_2$ in the formula (1) are preferably the same substituted or unsubstituted 2-benzo[b]thienyl groups, the same substituted or unsubstituted 2-benzo[b]furanyl groups, or the same substituted or unsubstituted 2-benzo[d]thiazole groups, more preferably the same unsubstituted benzo[b]thienyl groups, the same unsubstituted 2-benzo[b]furanyl groups, or the same unsubstituted 2-benzo[d]thiazole groups, further preferably the same unsubstituted 2-benzo[d]thiazole groups.

The positions of substitution of the phenyl groups in the formula (1) described above are not particularly limited and are preferably the 2,7-positions in [1]benzothieno[3,2-b][1]benzothiophene in the formula (1). Specifically, the compound represented by the formula (1) is preferably a compound represented by the following general formula (2):

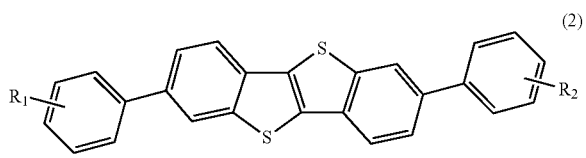

(2)

In the formula (2), $R_1$ and $R_2$ are the same as $R_1$ and $R_2$ defined in the formula (1). Preferred $R_1$ and $R_2$ are also the same as in the formula (1).

Specifically, the compound represented by the formula (2) is preferably a compound of the formula (2) wherein both of $R_1$ and $R_2$ take the "preferred" to "most preferred" forms in the formula (1) described above.

The position of substitution of each of $R_1$ and $R_2$ in the formula (2) described above is not particularly limited and is preferably the para position of each phenyl group, which is a substituent on [1]benzothieno[3,2-b][1]benzothiophene in the formula (2). Specifically, the compound represented by the formula (2) is preferably a compound represented by the following general formula (3):

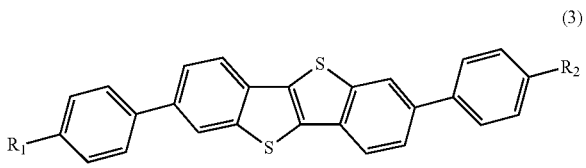

(3)

In the formula (3), $R_1$ and $R_2$ are the same as $R_1$ and $R_2$ defined in the formula (1). Preferred $R_1$ and $R_2$ are also the same as in the formula (1).

Specifically, the compound represented by the formula (3) is preferably a compound of the formula (3) wherein both of $R_1$ and $R_2$ take the preferred to most preferred forms in the formula (1) described above.

Specific examples of the compound represented by the formula (1) will be illustrated below. However, the present invention is not limited by these specific examples.

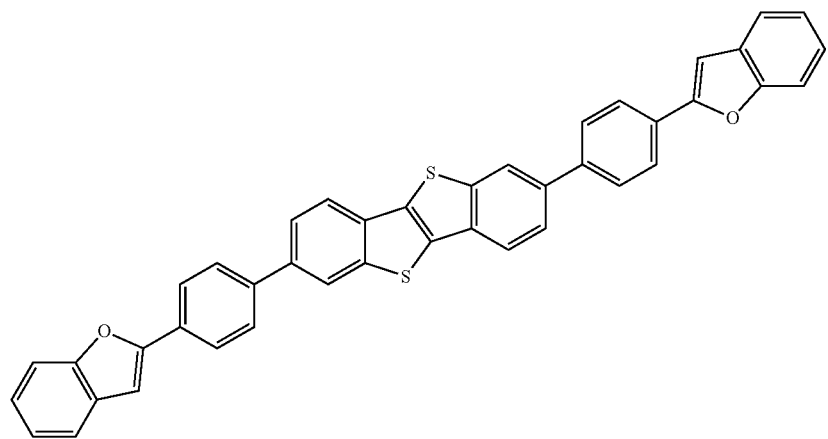
No. 1
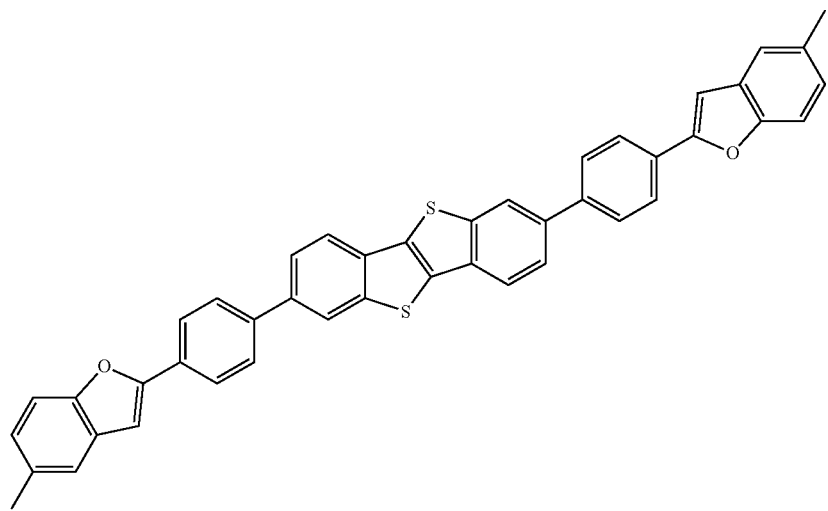
No. 2
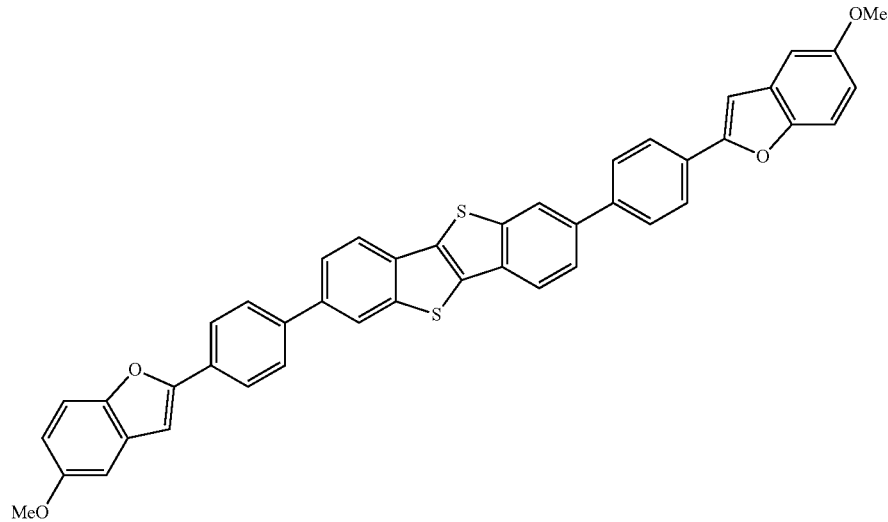
No. 3

No. 4
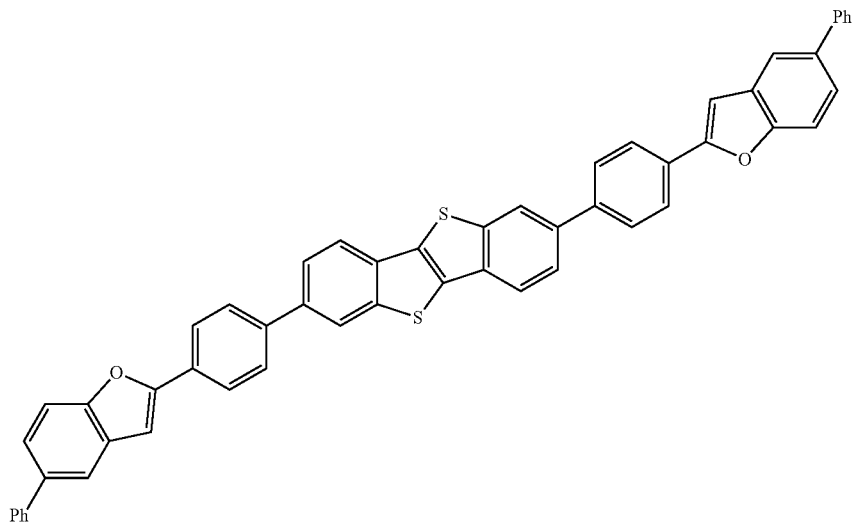
No. 5
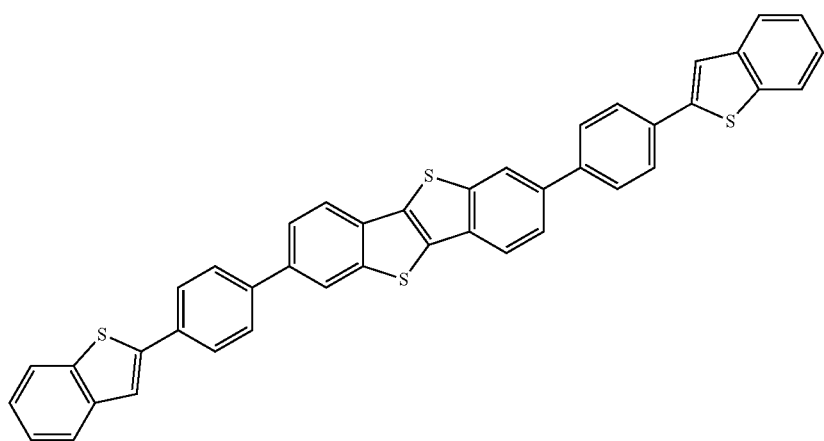
No. 6
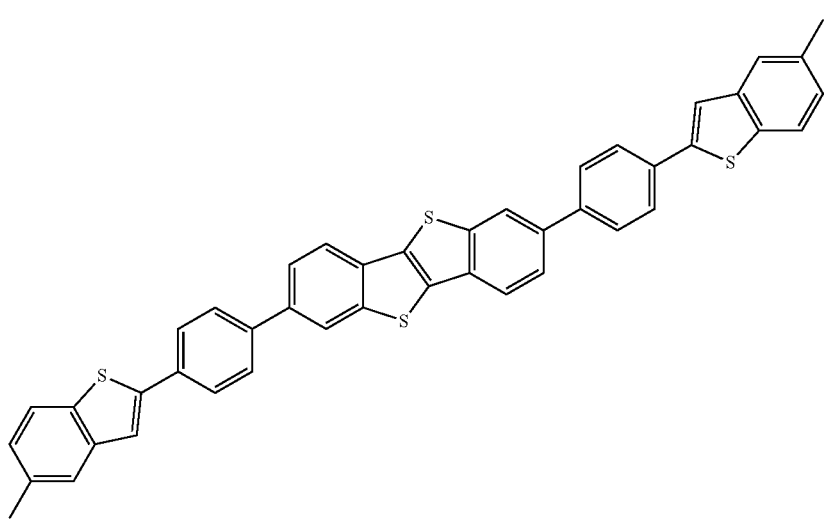

No. 7
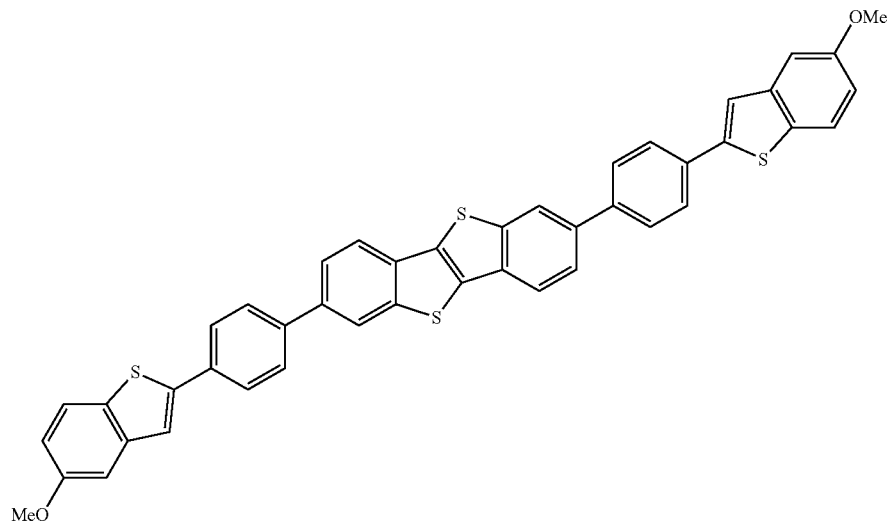
No. 8
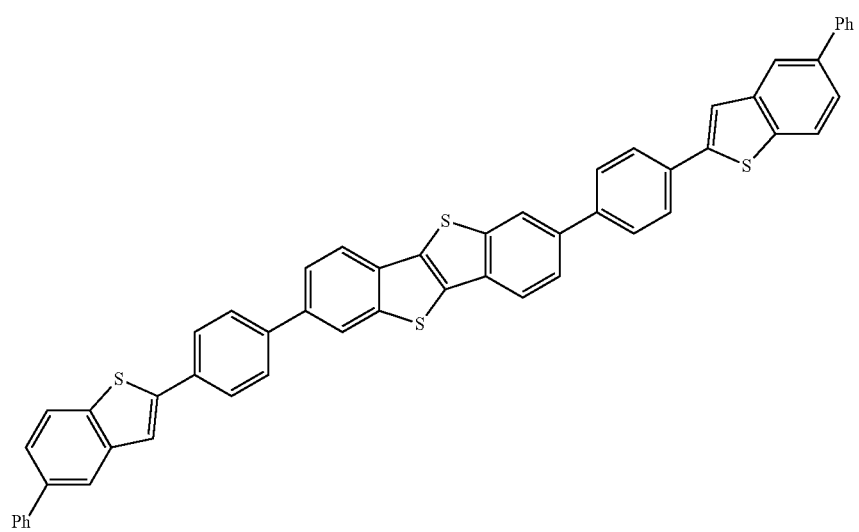
No. 9
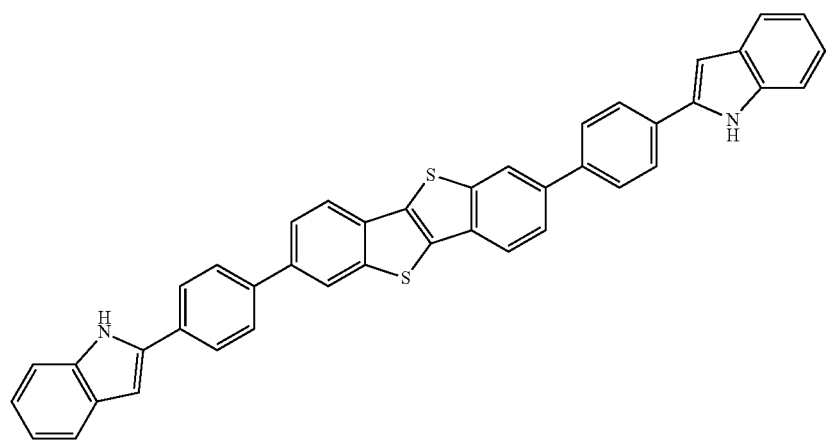

No. 10
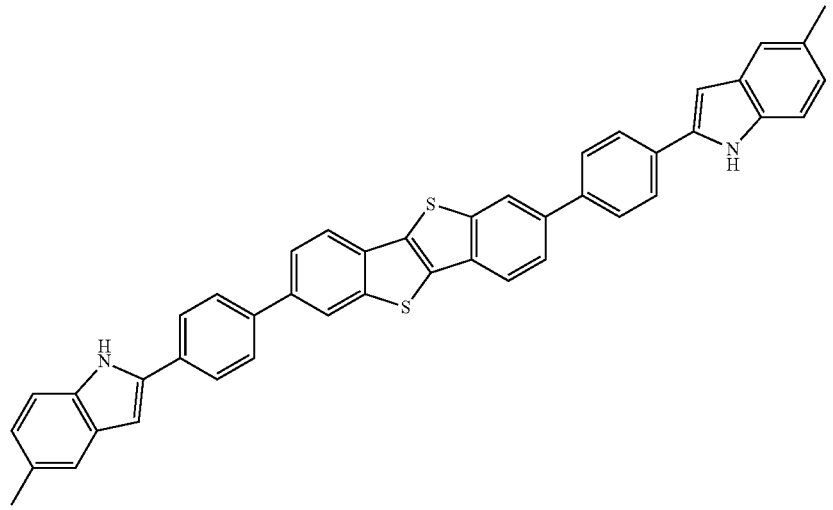
No. 11
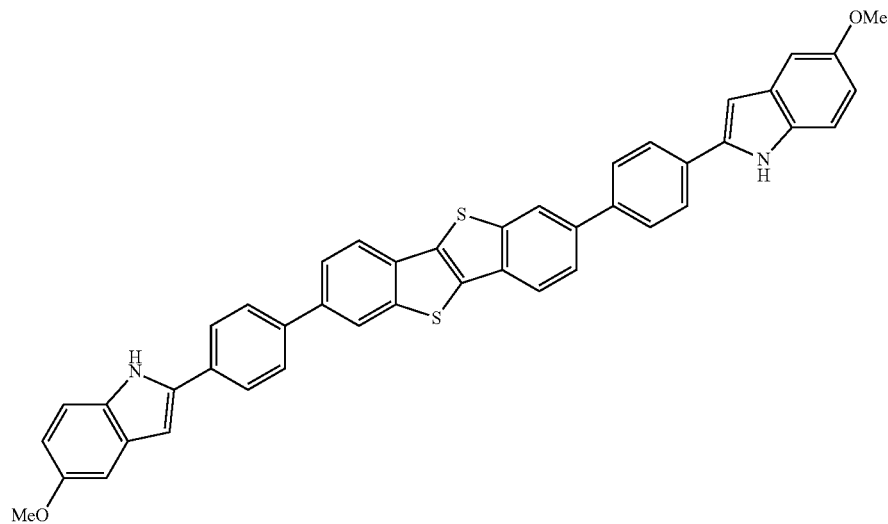
No. 12
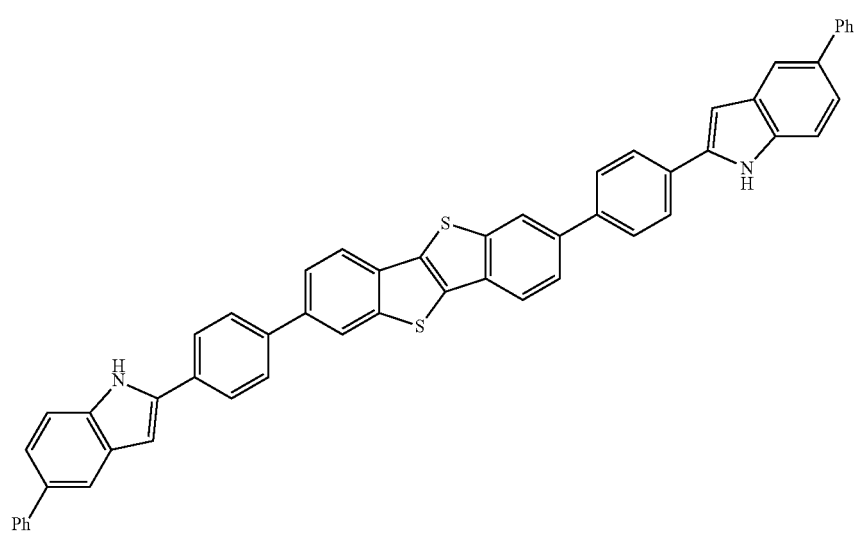

-continued
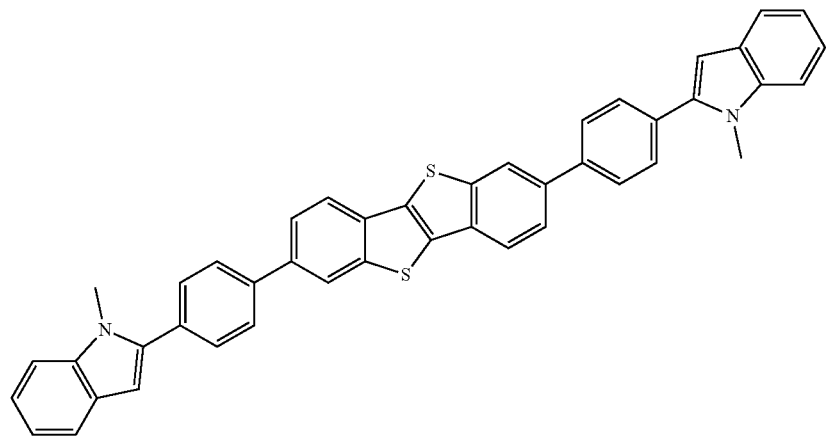
No. 13
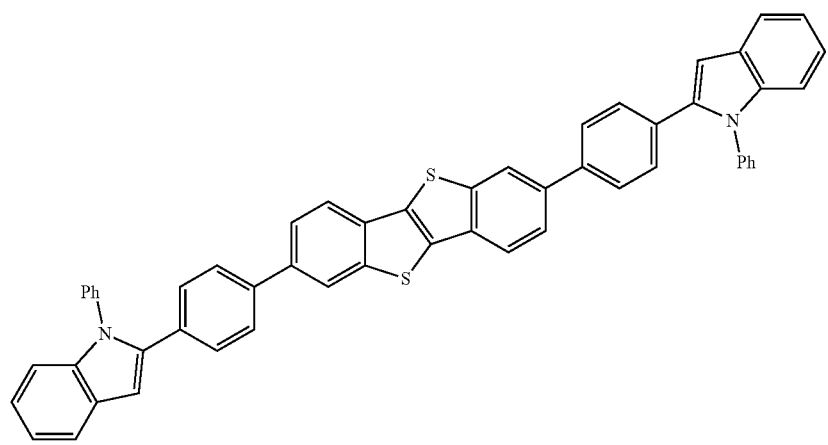
No. 14
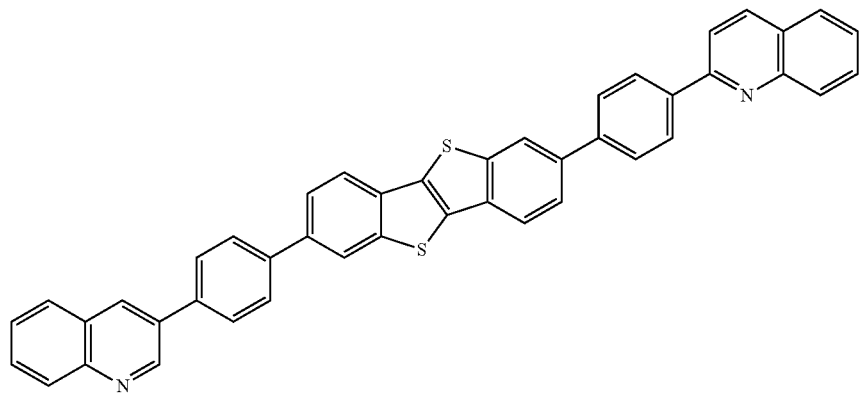
No. 15

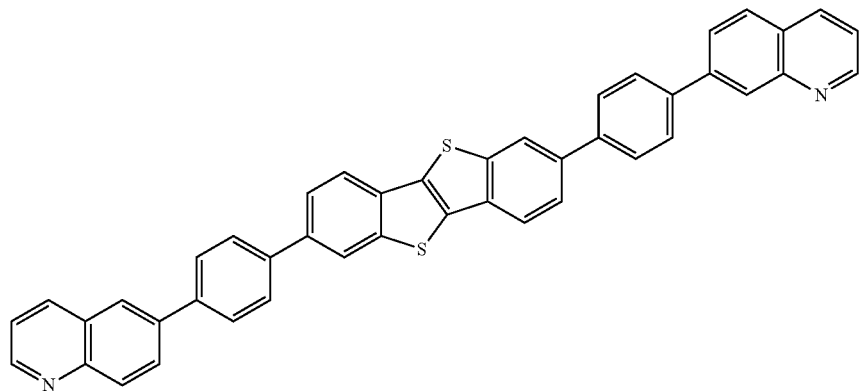
No. 16
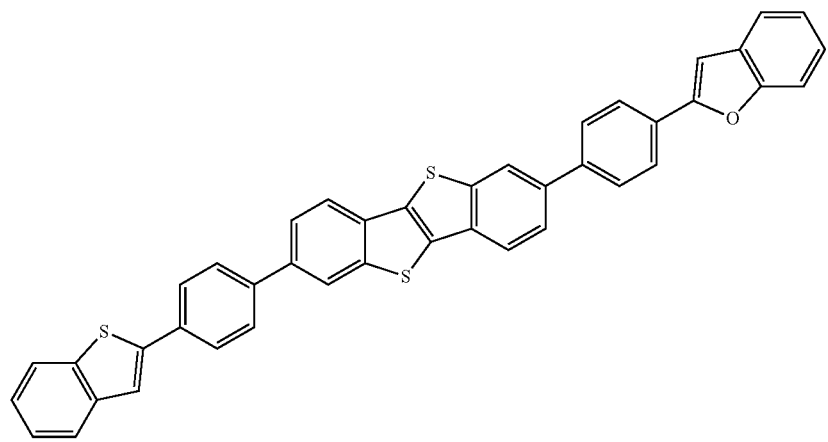
No. 17
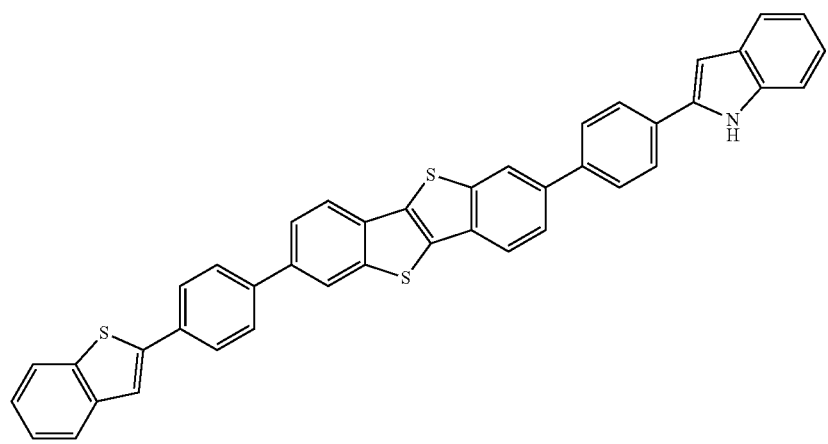
No. 18

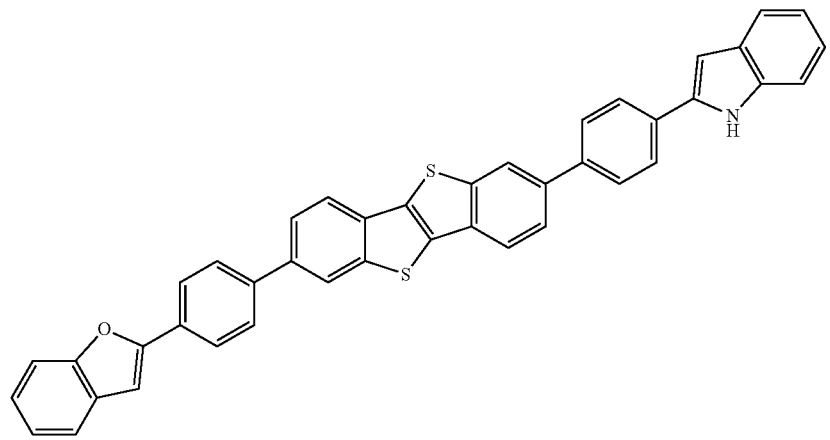
No. 19
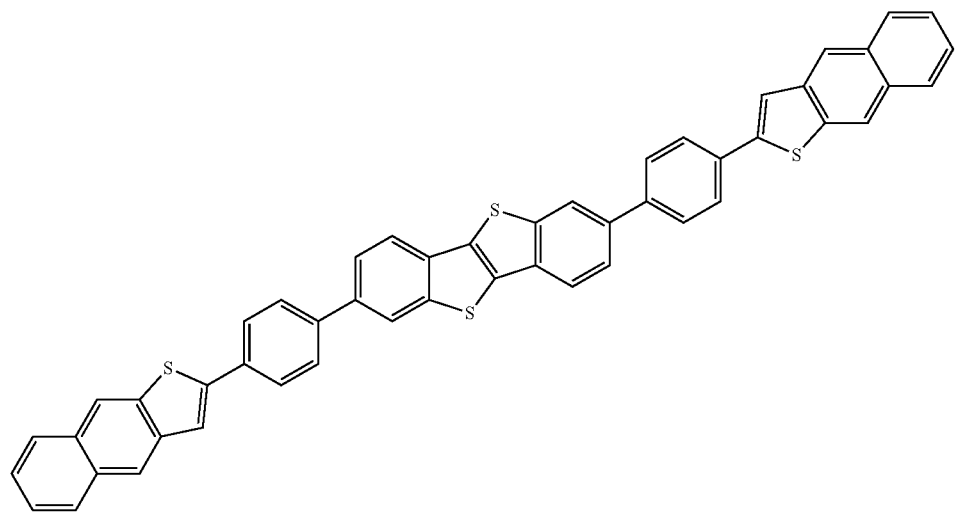
No. 20
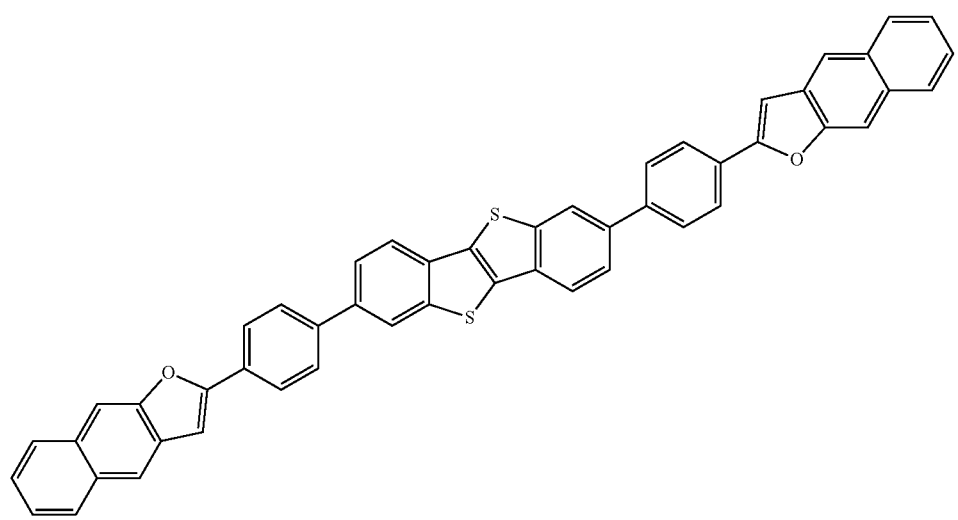
No. 21

-continued
No. 22
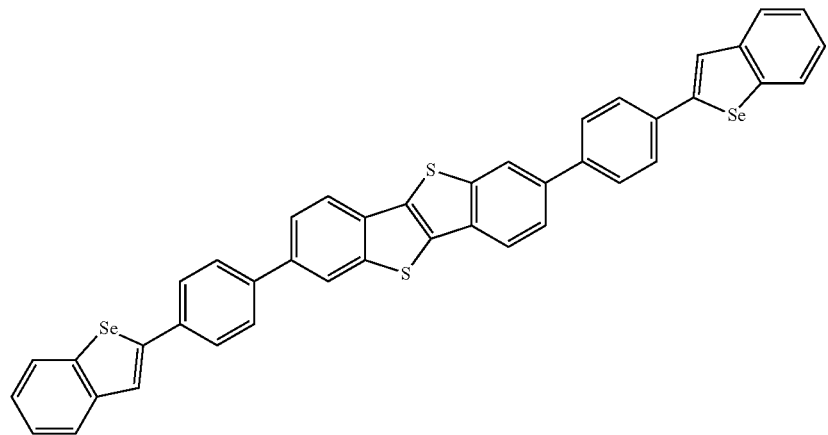
No. 23
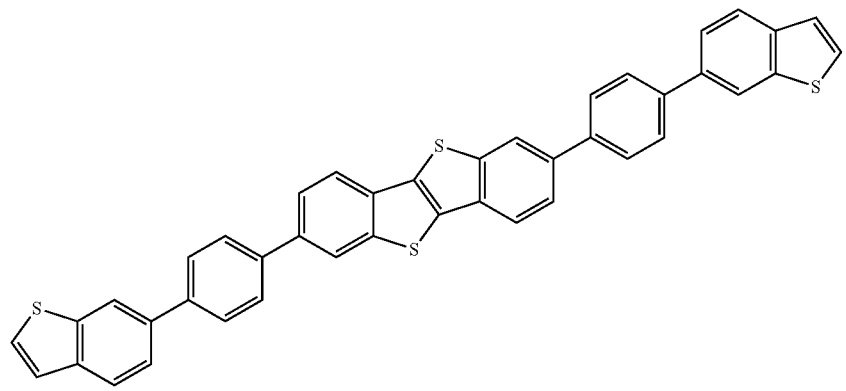
No. 24
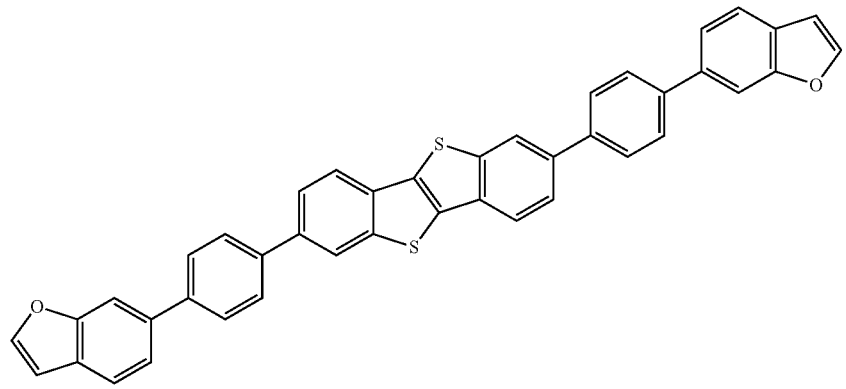
No. 25 No. 26
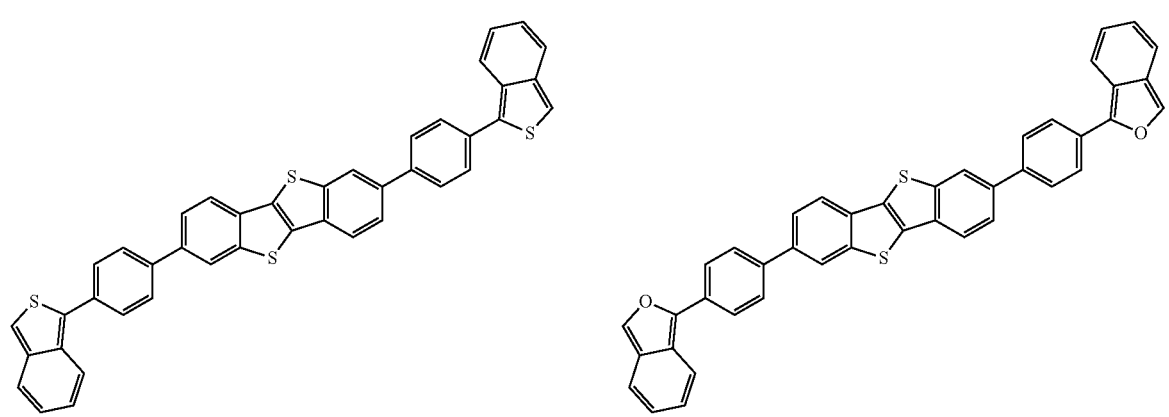

No. 27
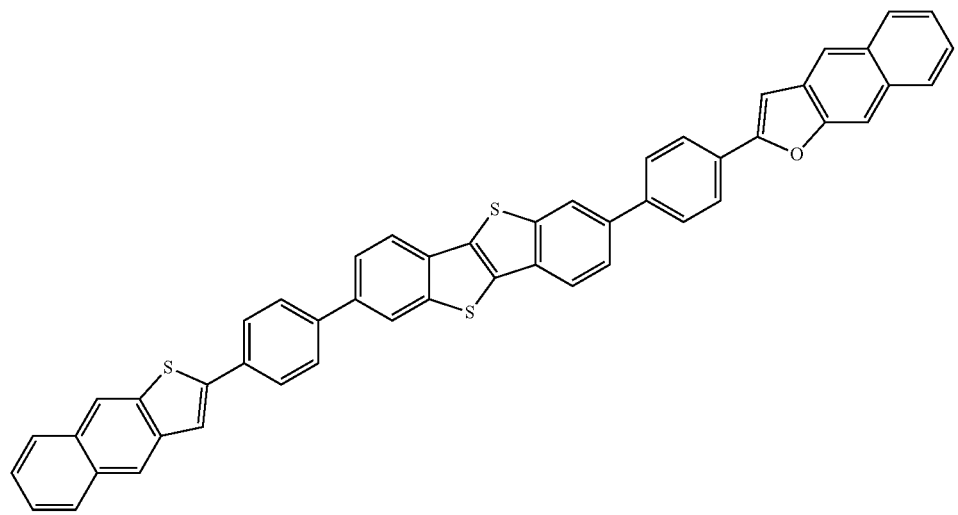
No. 28
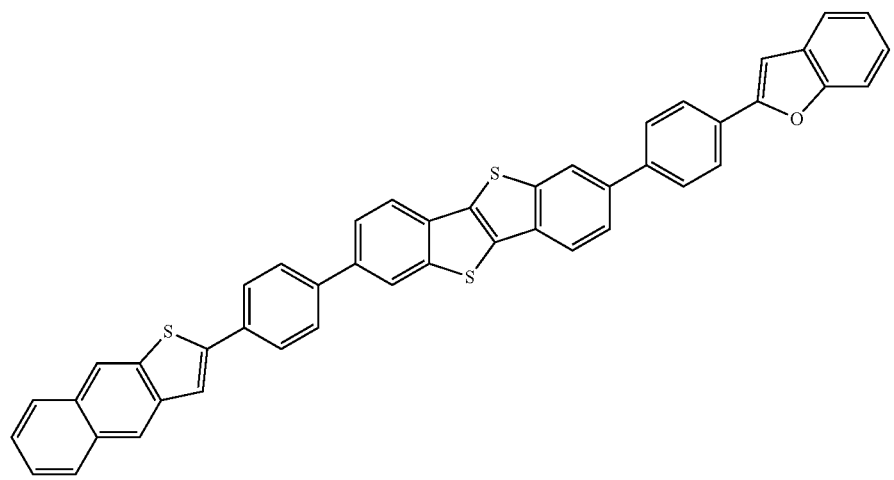
No. 29
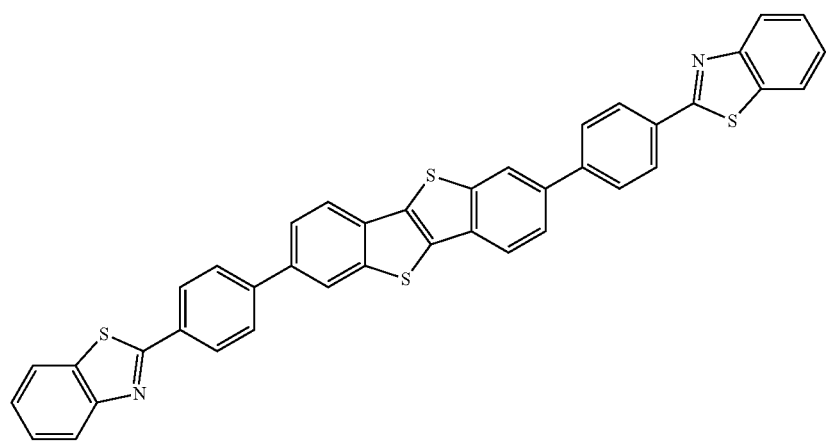

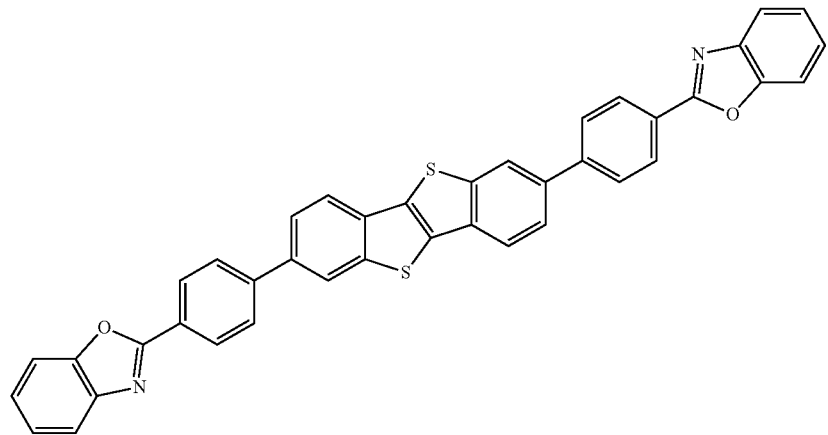
No. 30
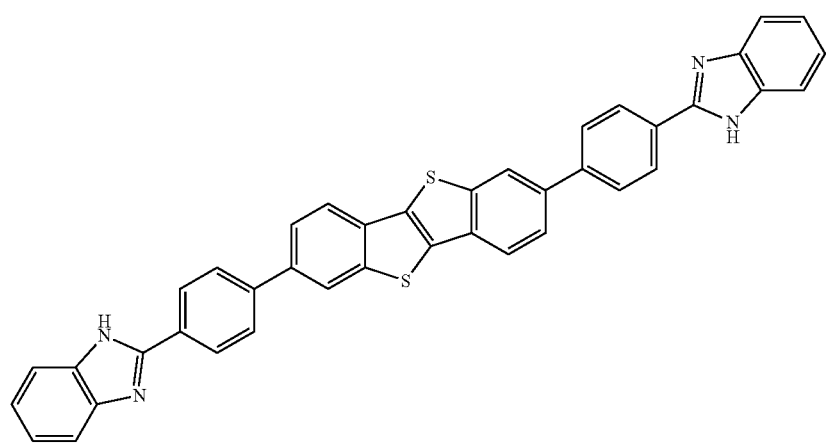
No. 31
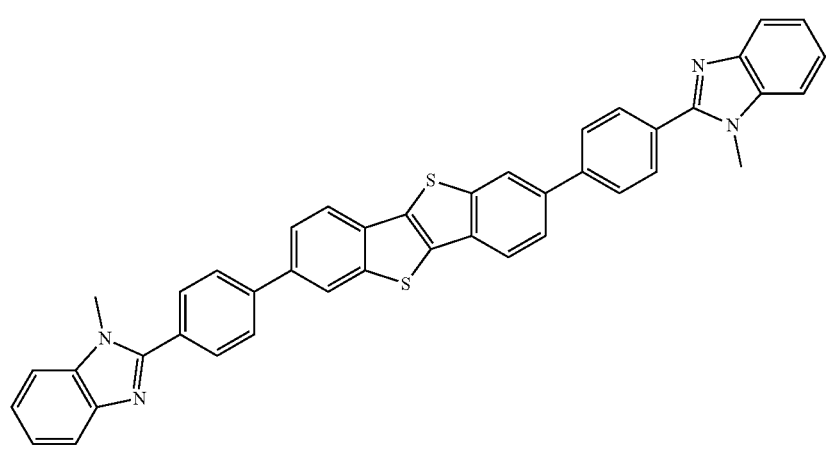
No. 32

-continued
No. 33
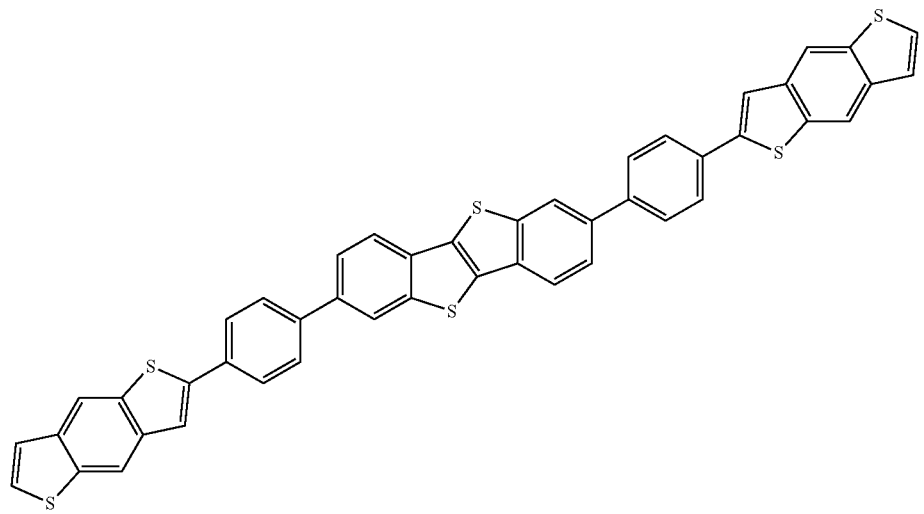
No. 34
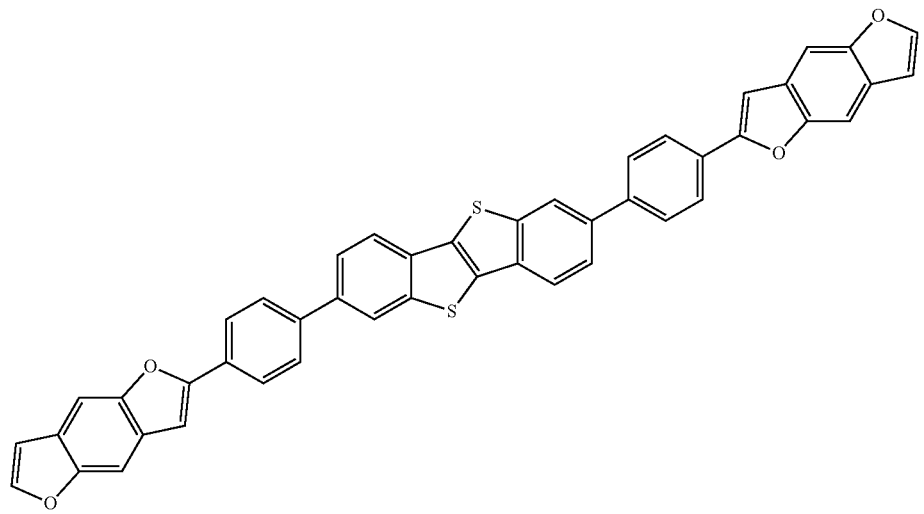
No. 35
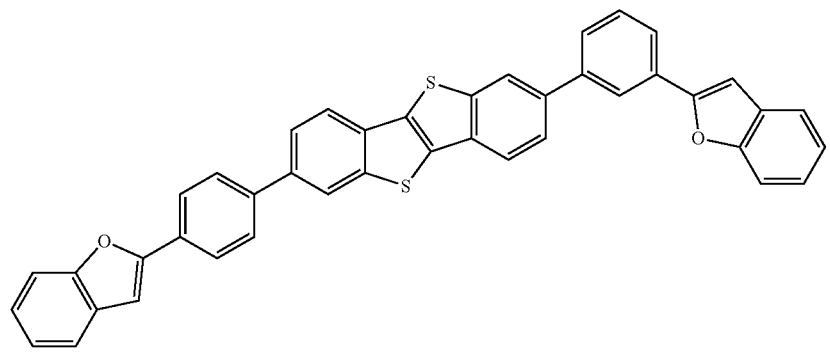
No. 36
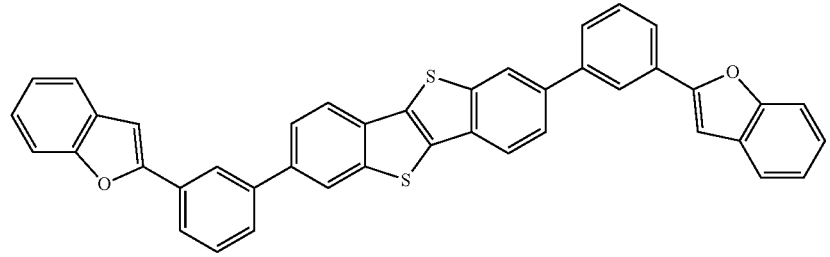

No. 37
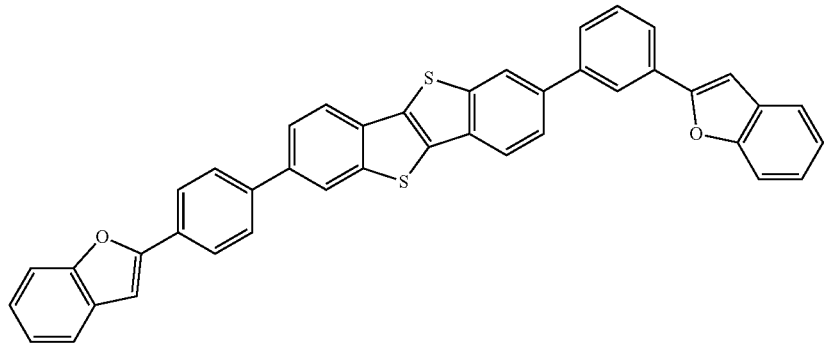
No. 38
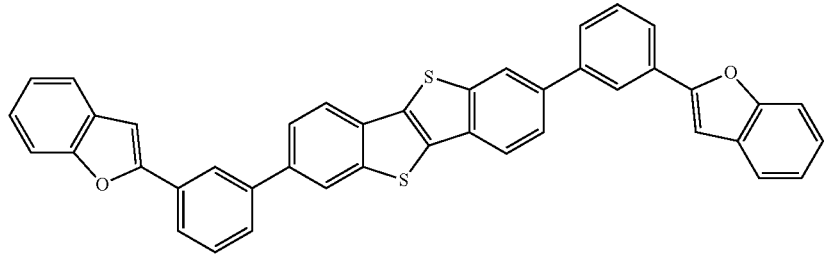
No. 39
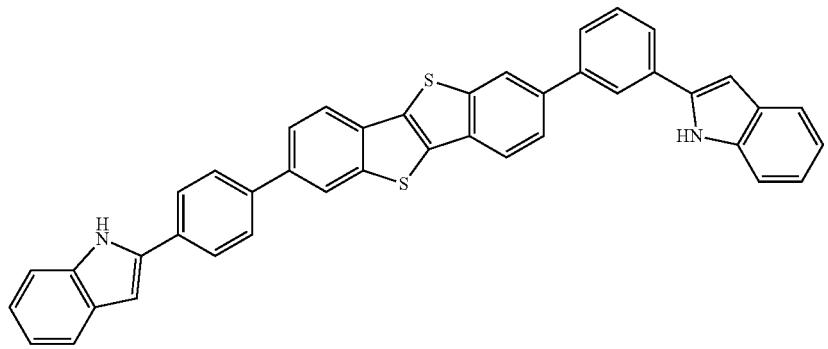
No. 40
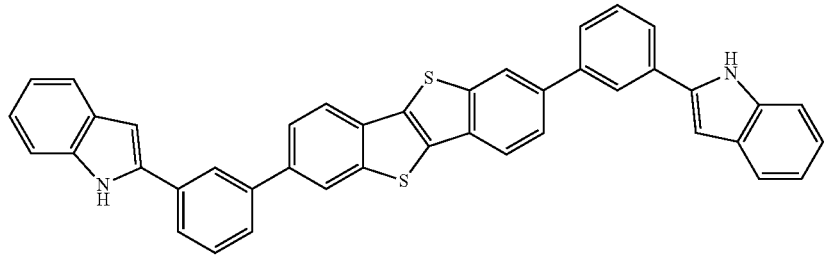
No. 41
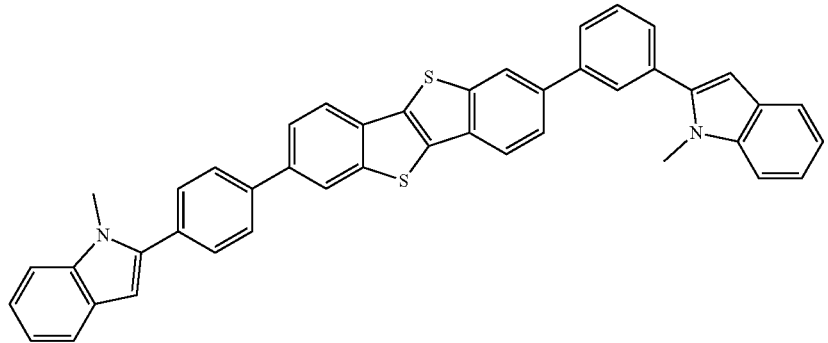

-continued
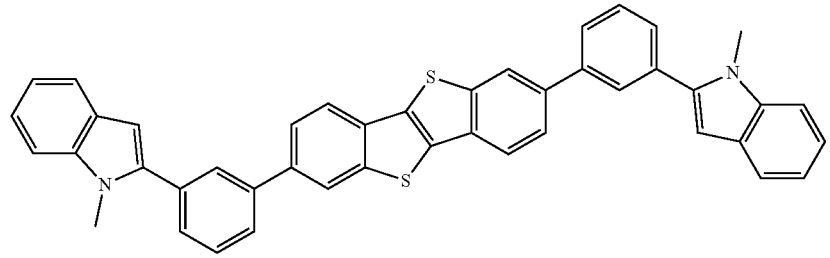
No. 42
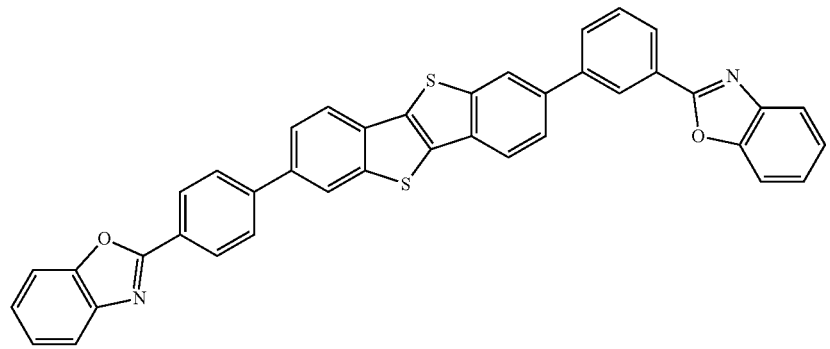
No. 43
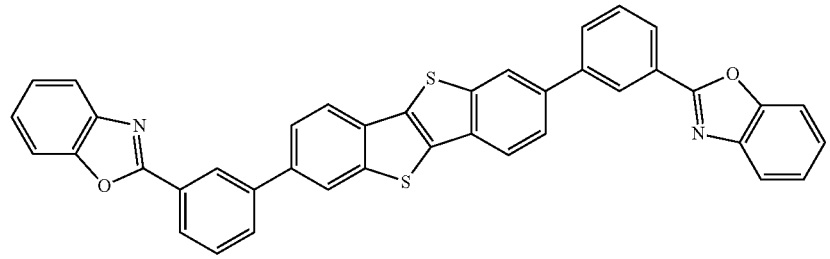
No. 44
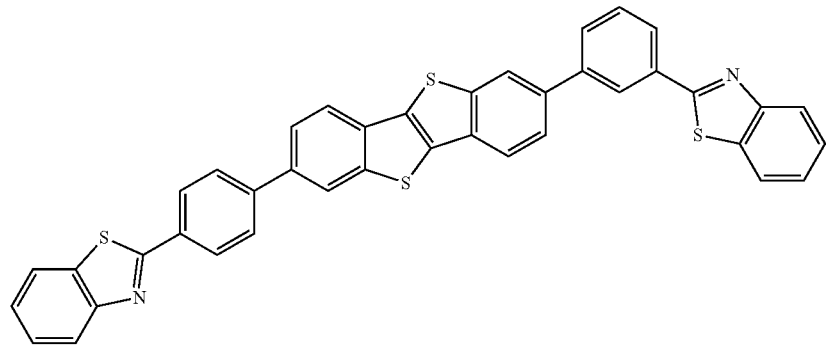
No. 45
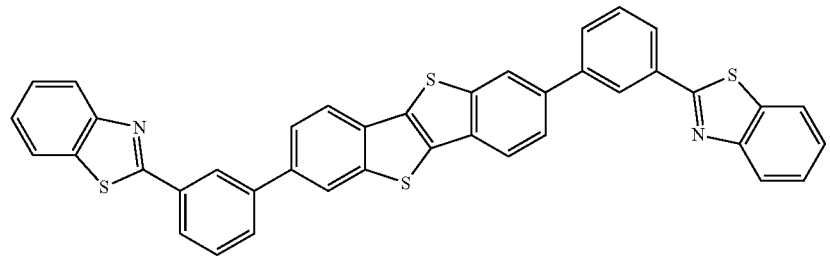
No. 46

-continued
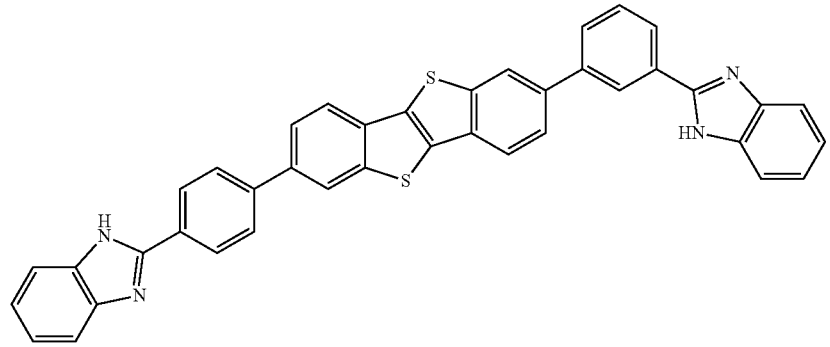
No. 47
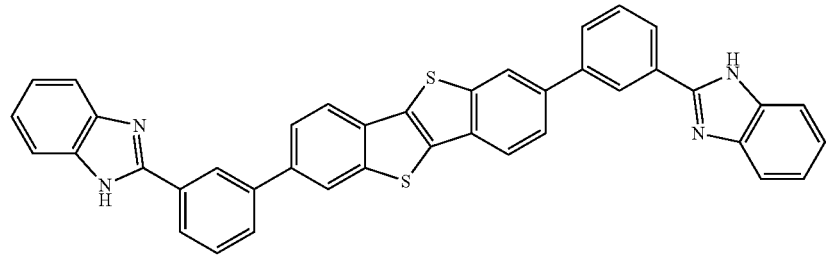
No. 48
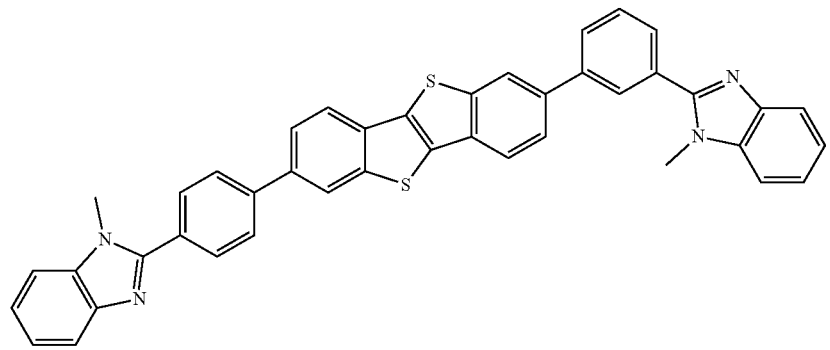
No. 49
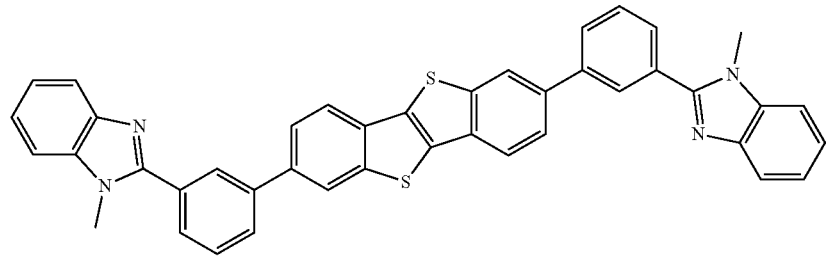
No. 50
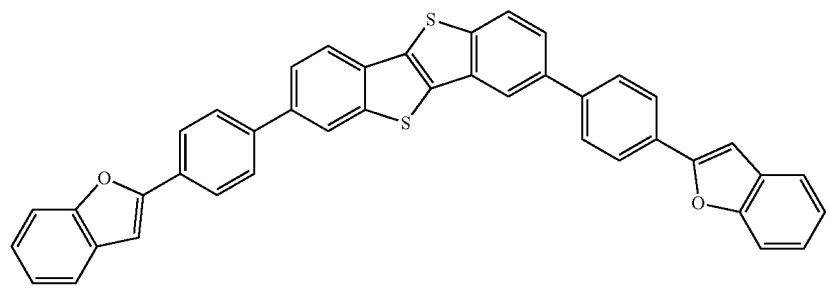
No. 51

-continued
No. 52
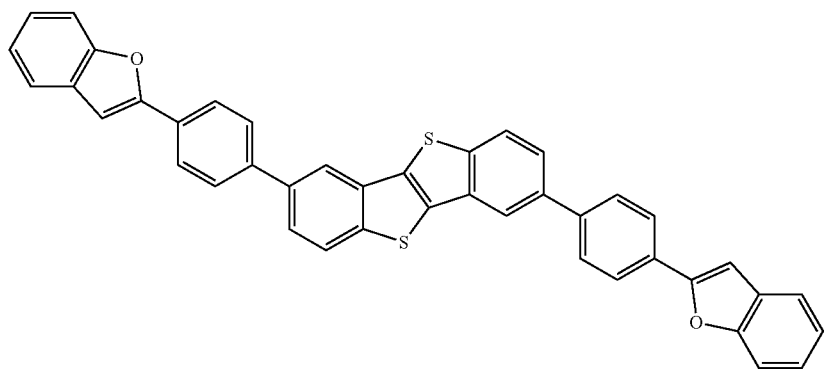
No. 53
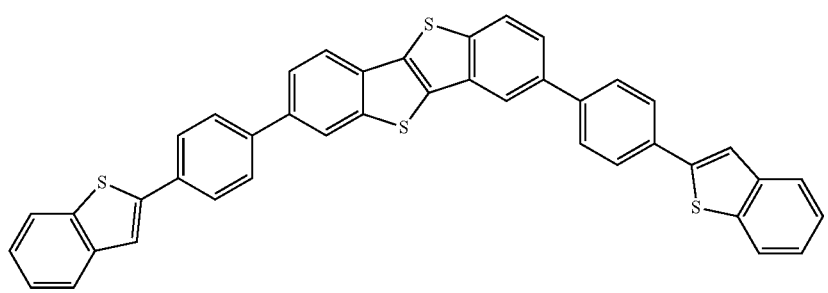
No. 54
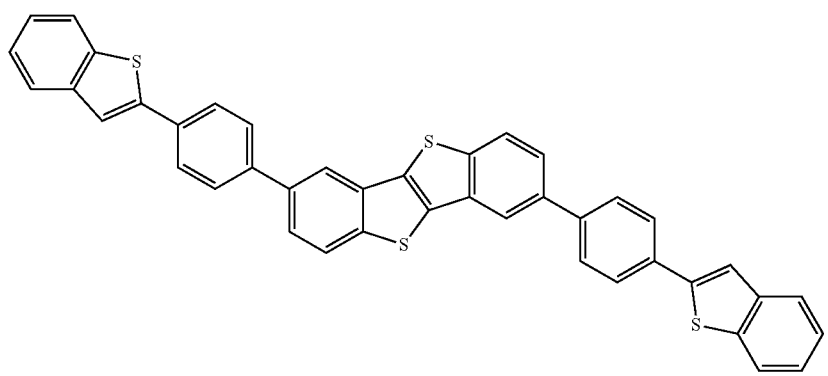
No. 55
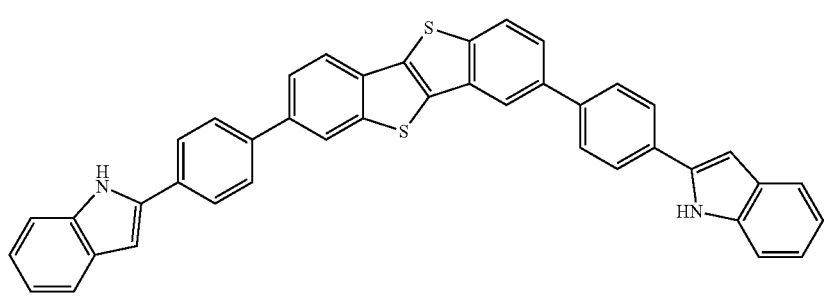

-continued
No. 56
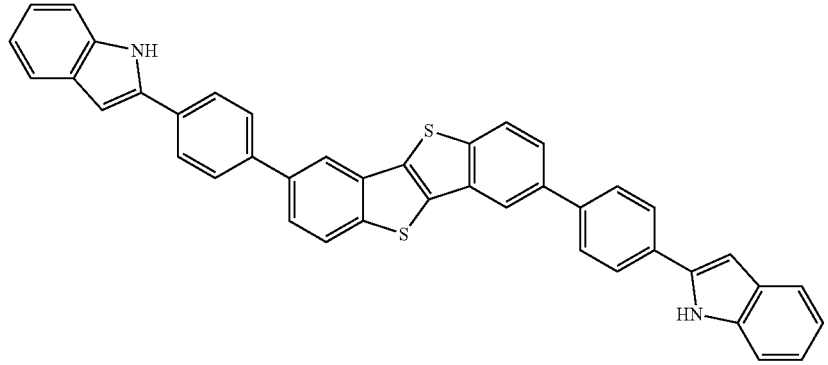
No. 57
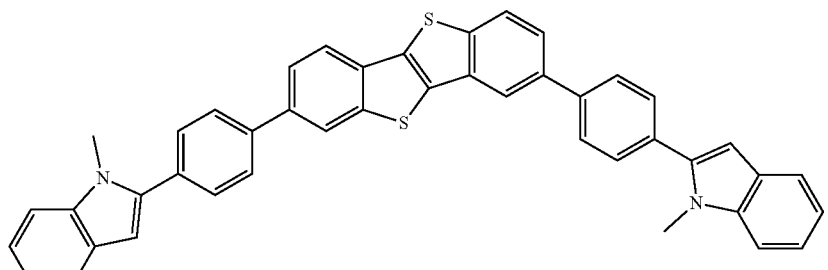
No. 58
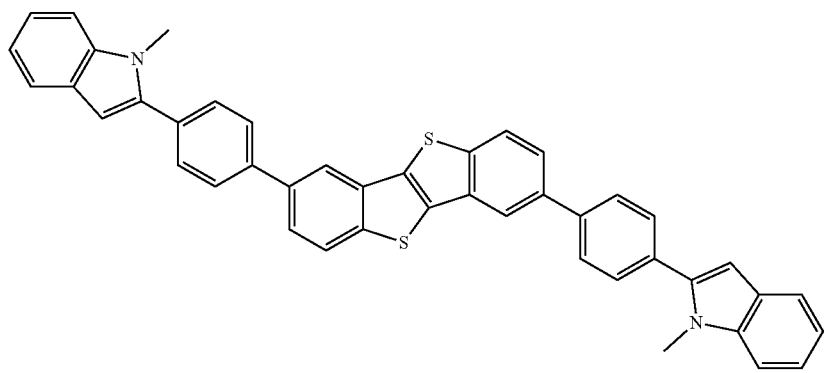
No. 59
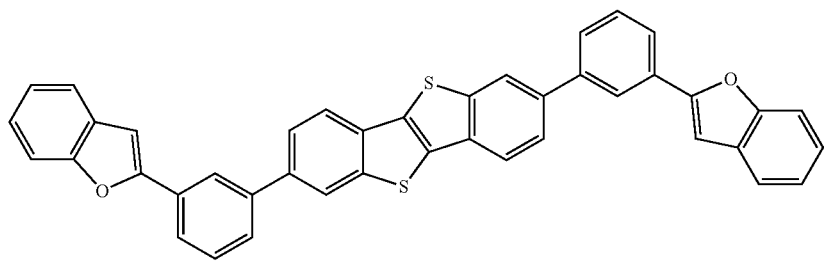
No. 60
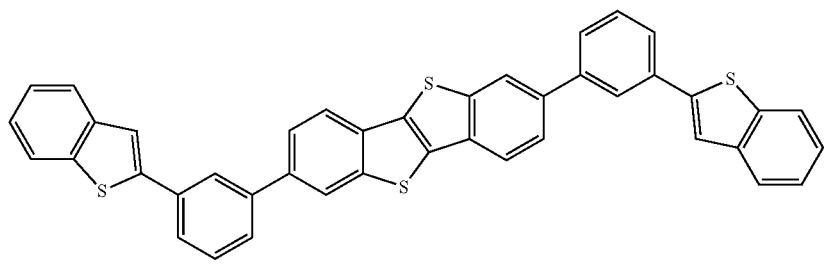

-continued
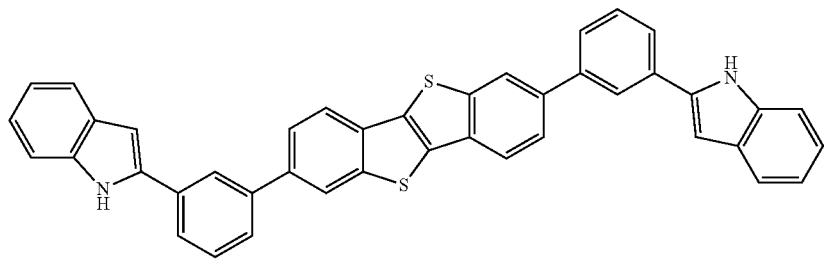
No. 61
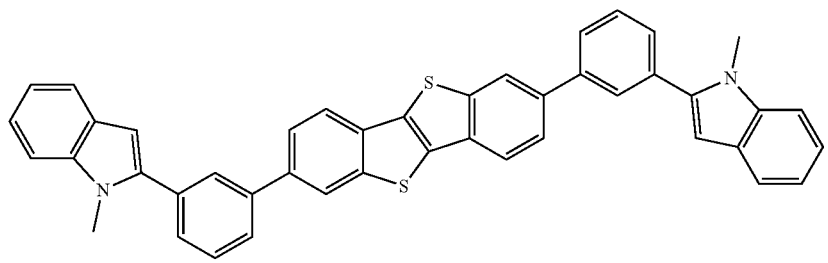
No. 62
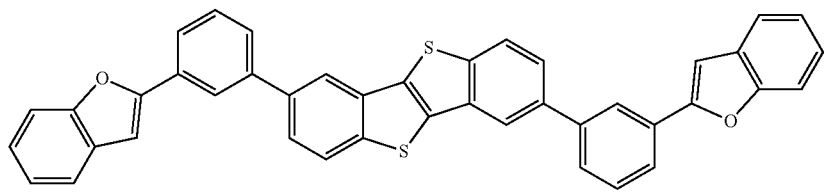
No. 63
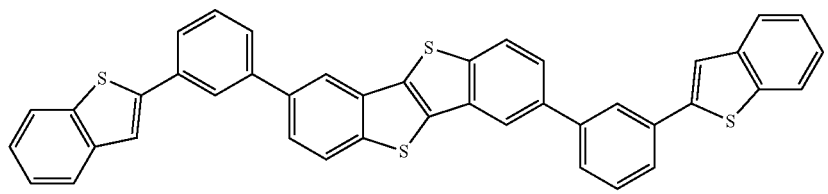
No. 64
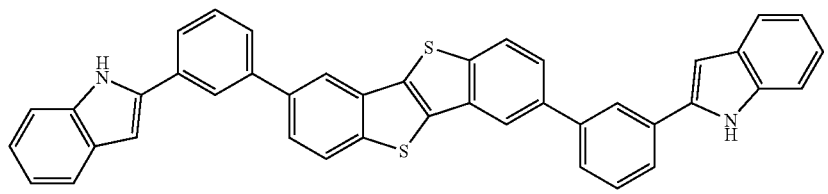
No. 65
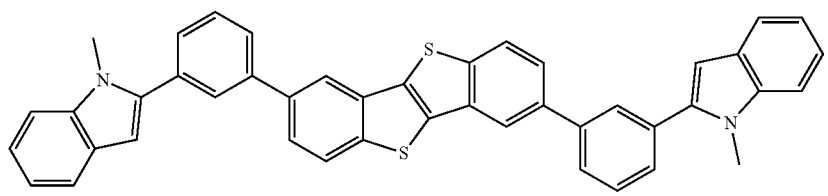
No. 66

-continued
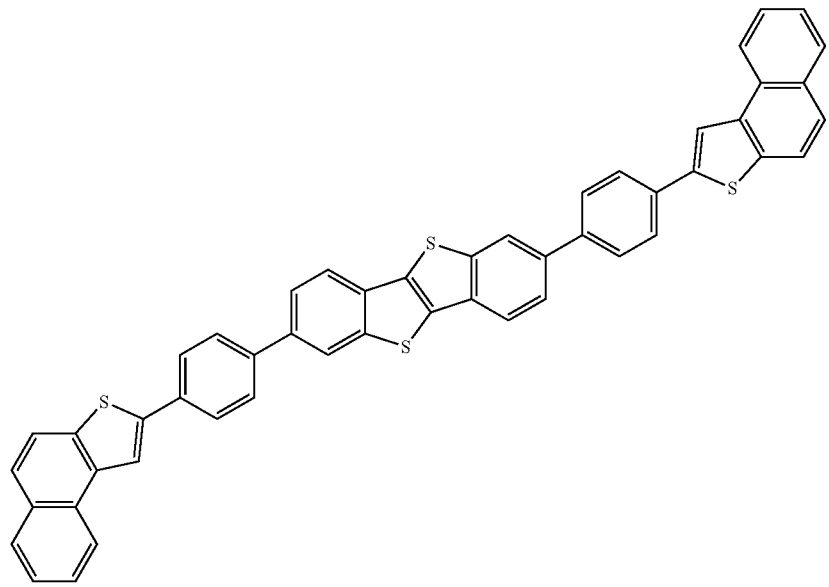
No. 67
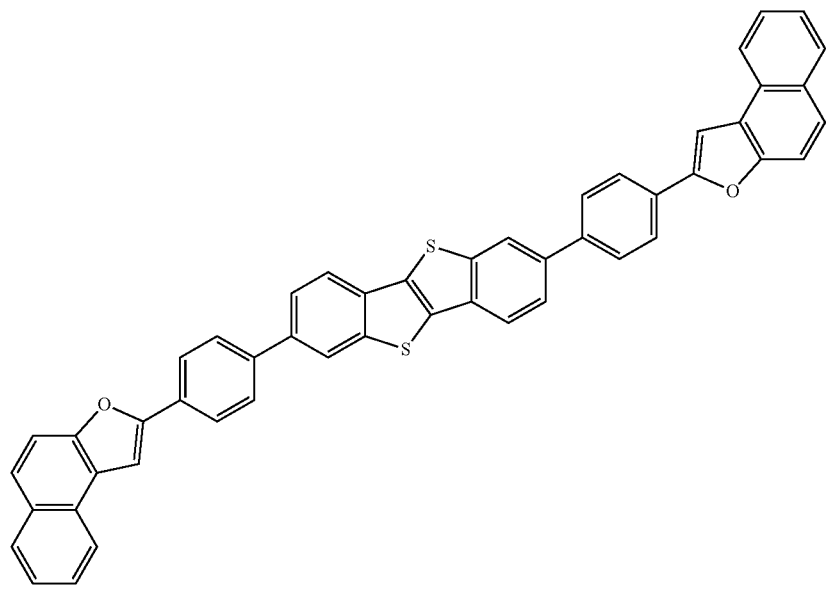
No. 68
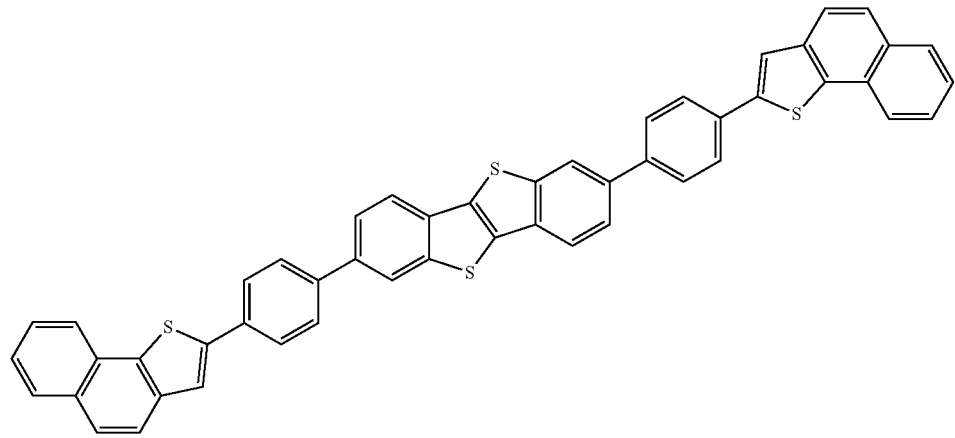
No. 69

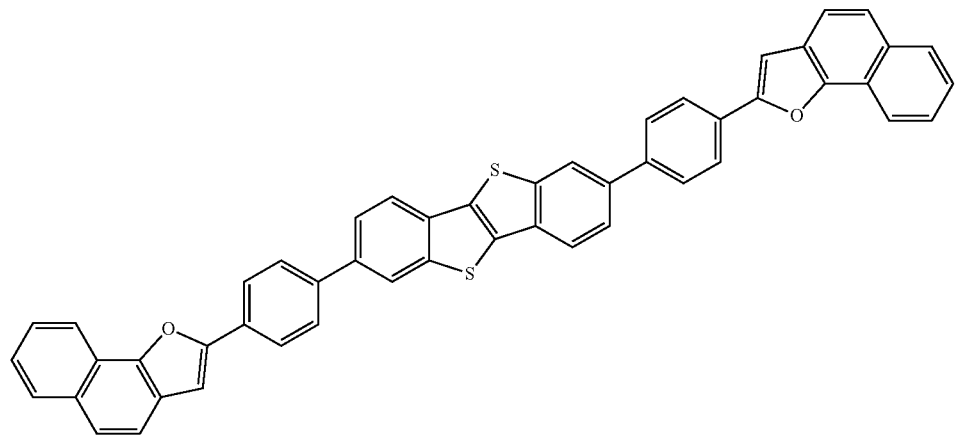
No. 70
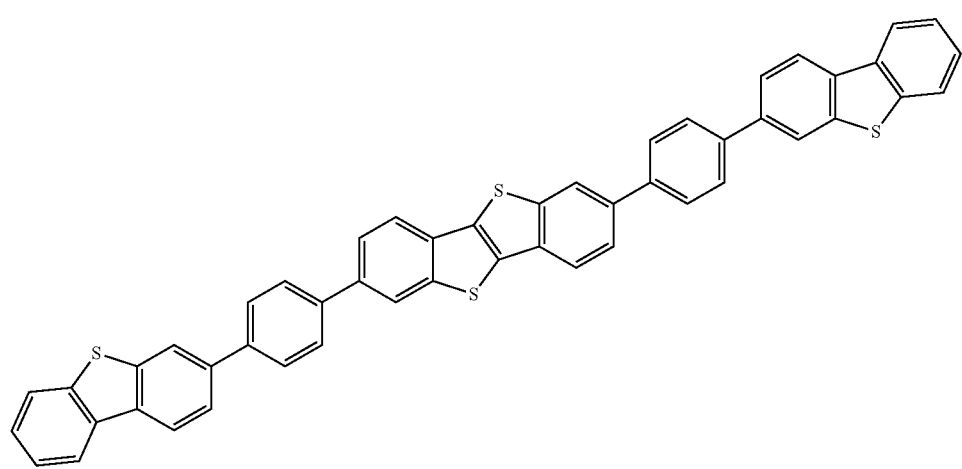
No. 71
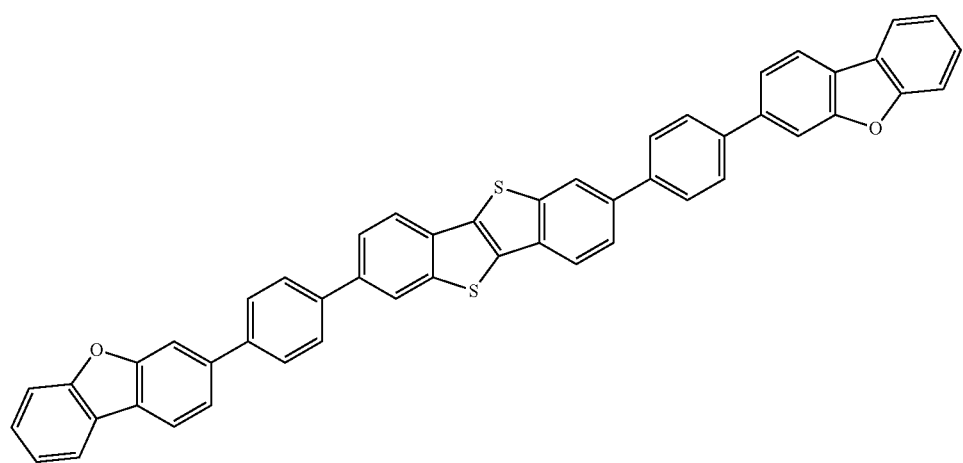
No. 72

-continued
No. 73
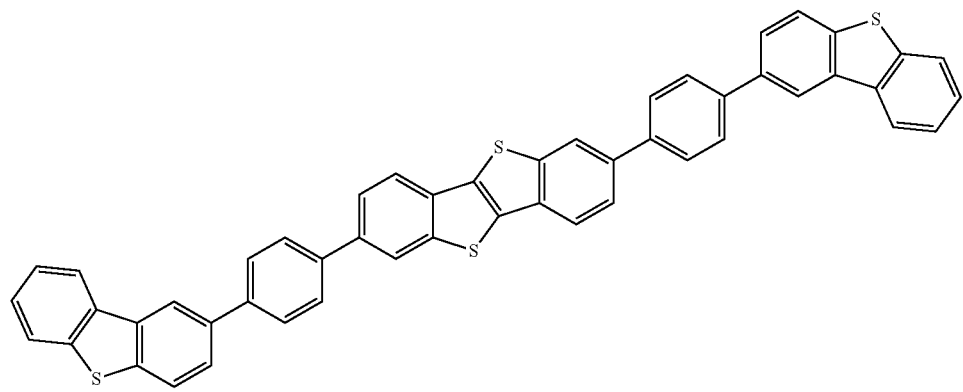
No. 74
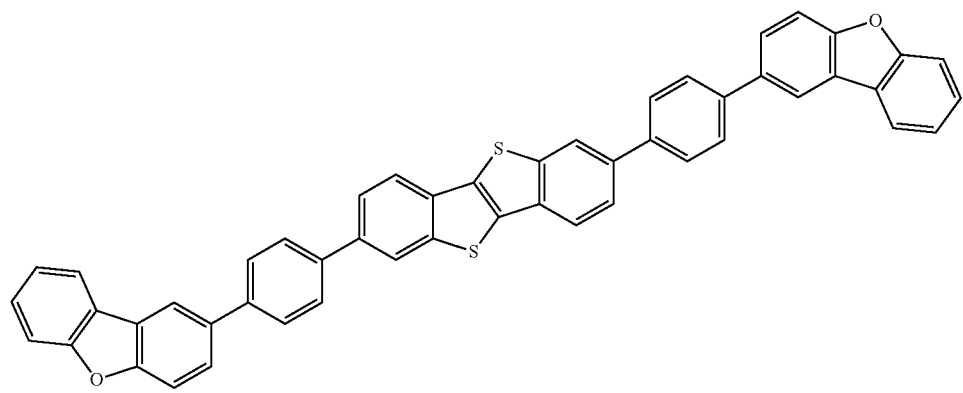
No. 75
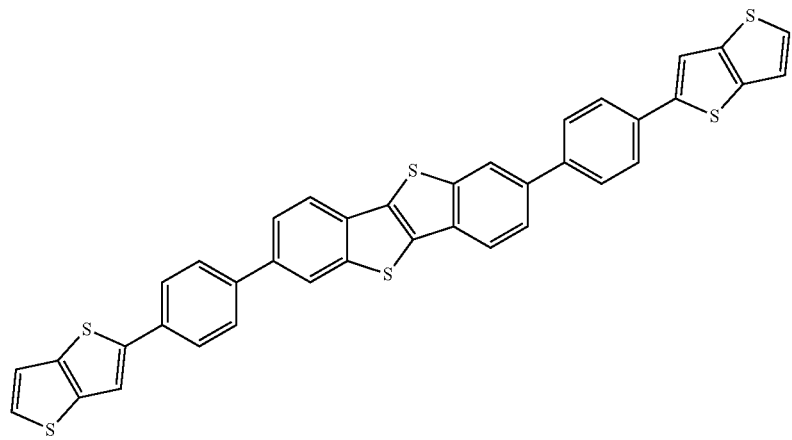
No. 76
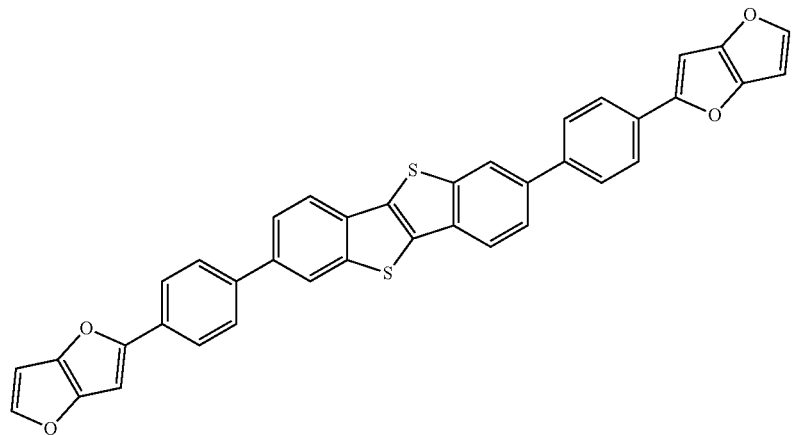

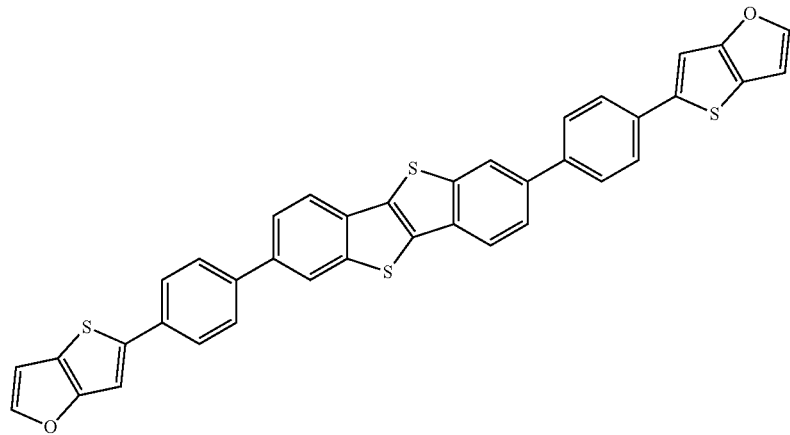
No. 77
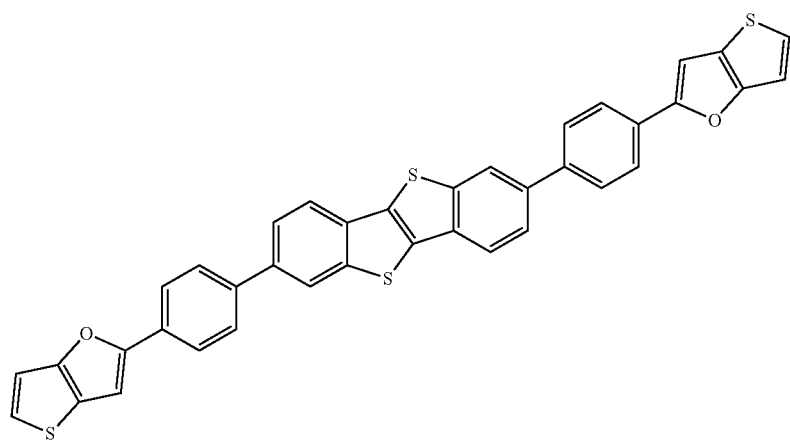
No. 78
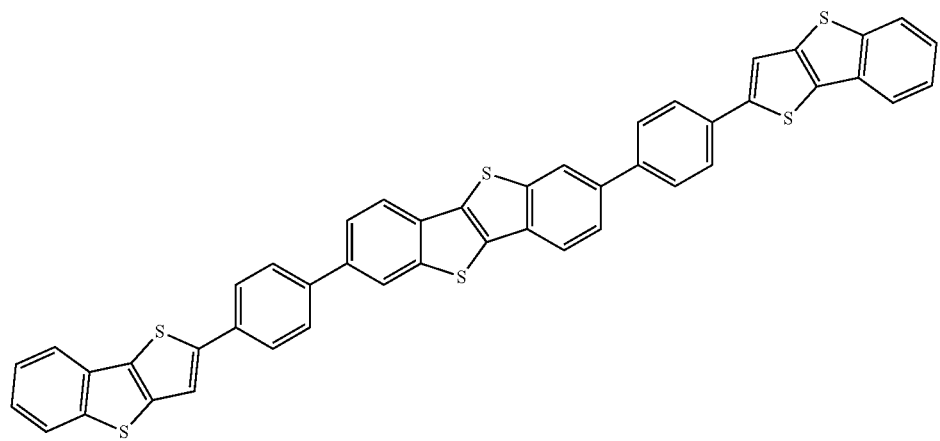
No. 79

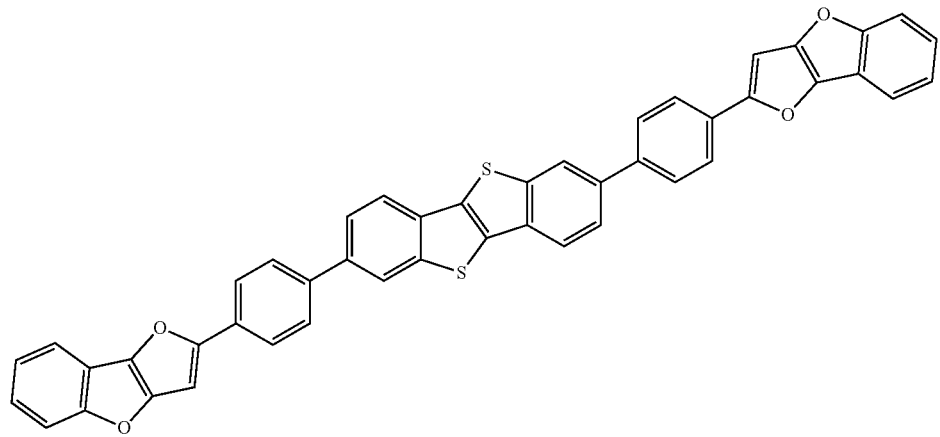
No. 80
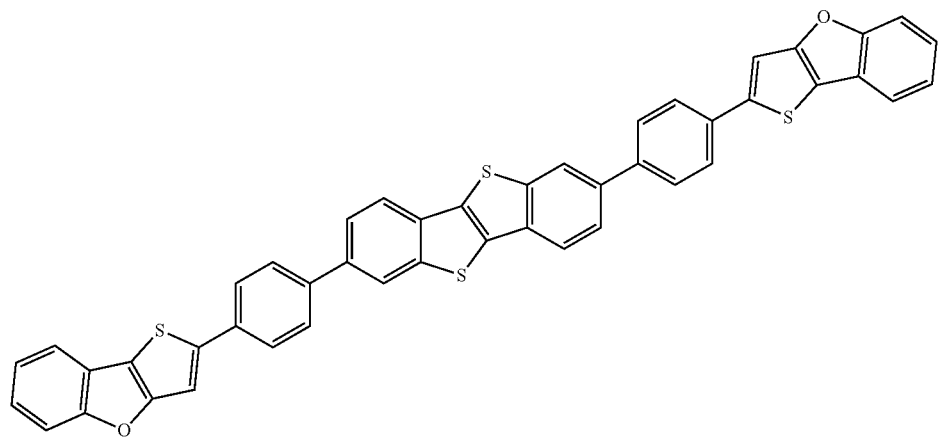
No. 81
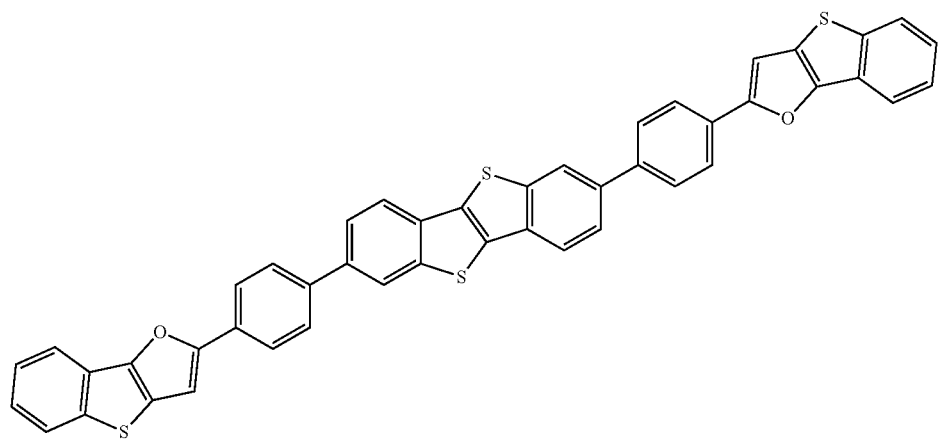
No. 82

No. 83
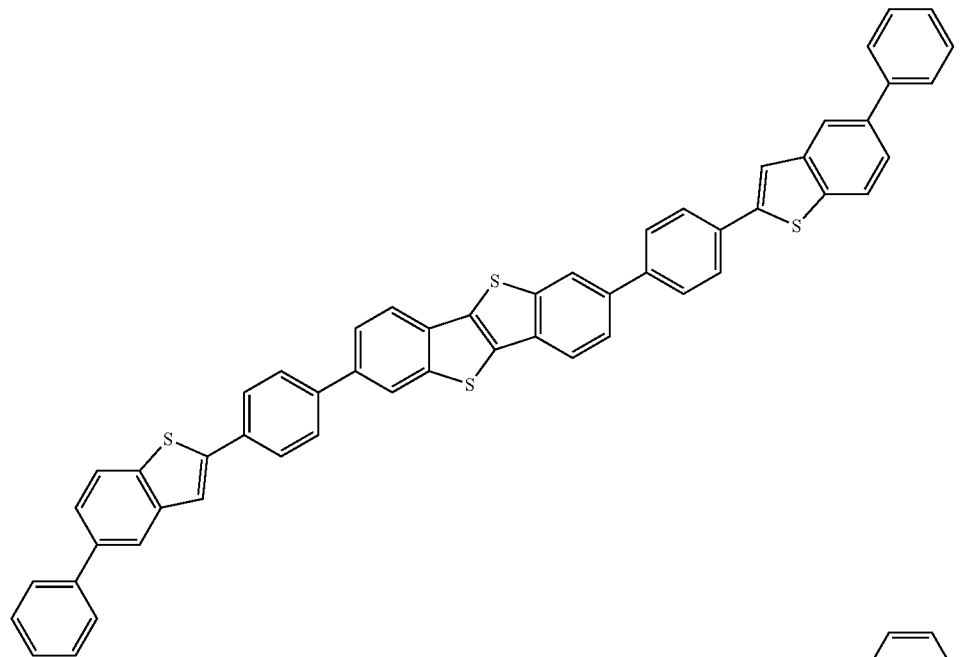
No. 84
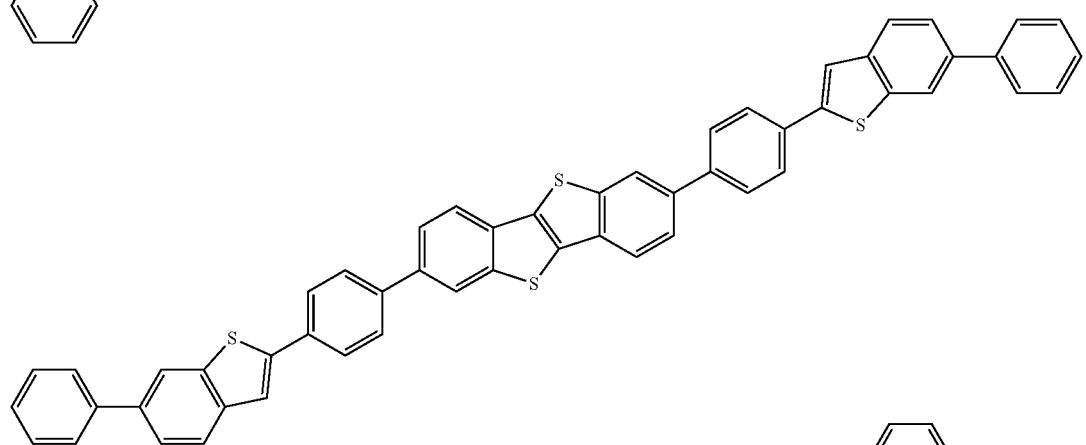
No. 85
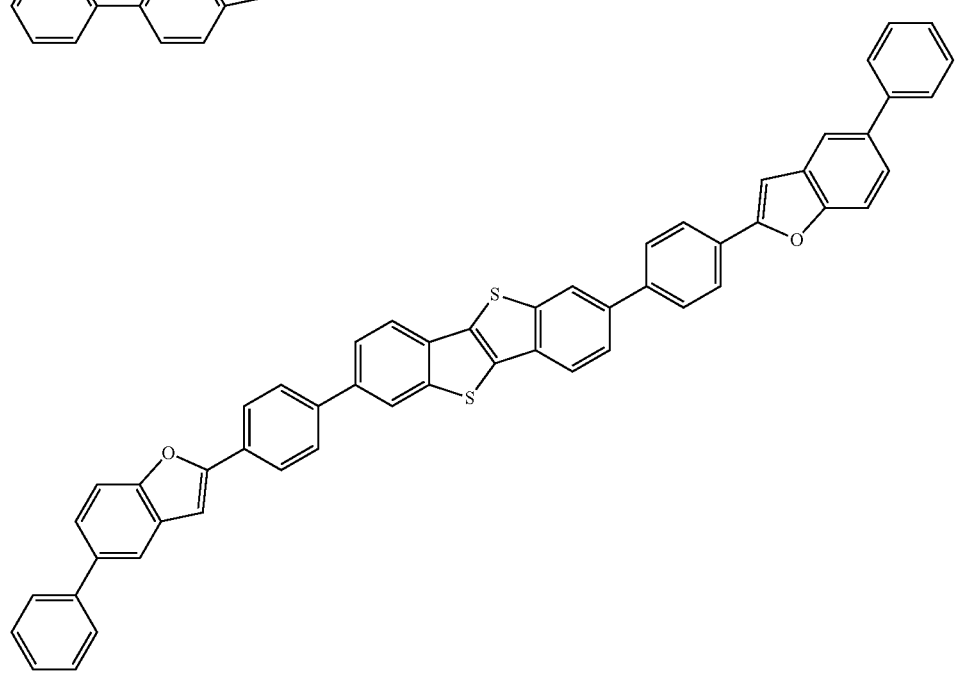

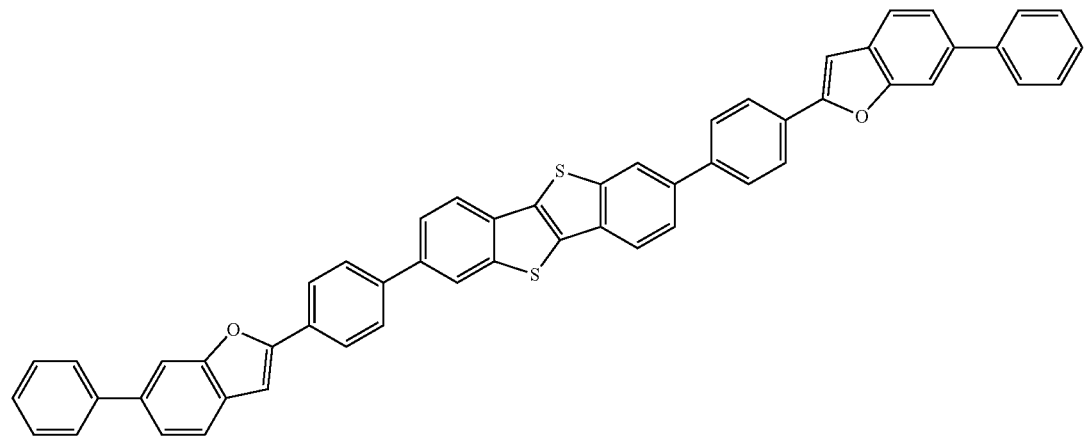
No. 86
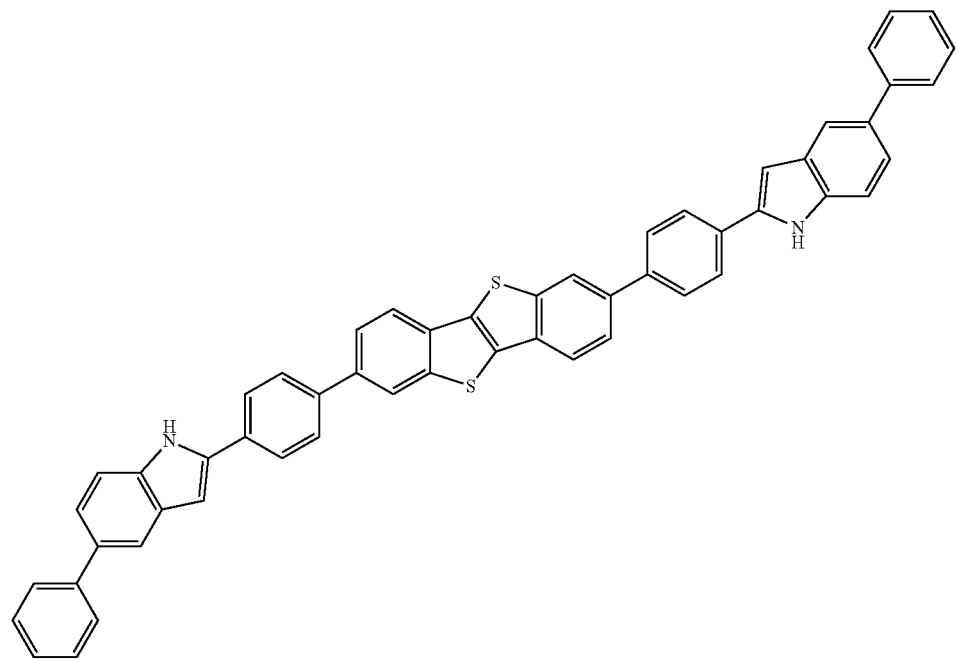
No. 87
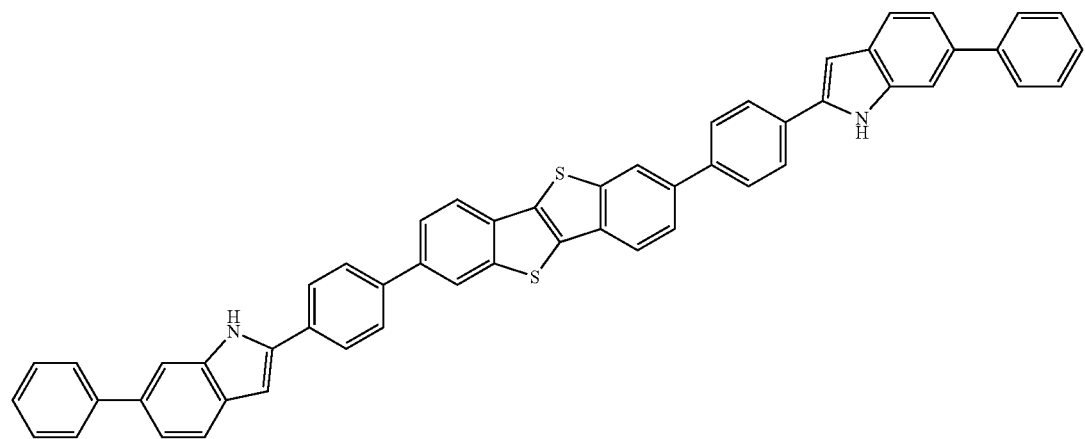
No. 88

-continued
No. 89
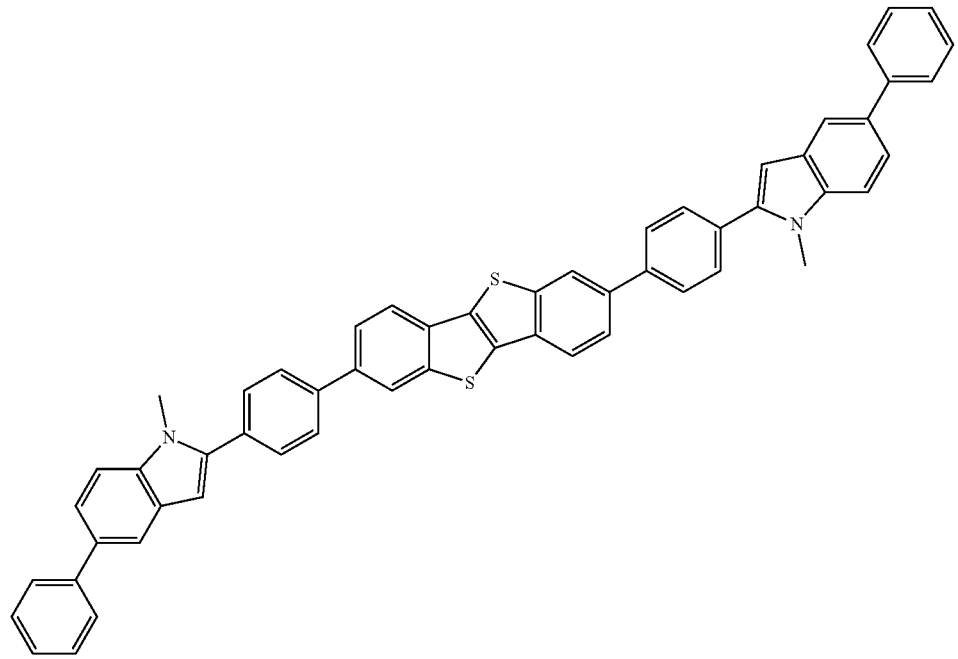
No. 90
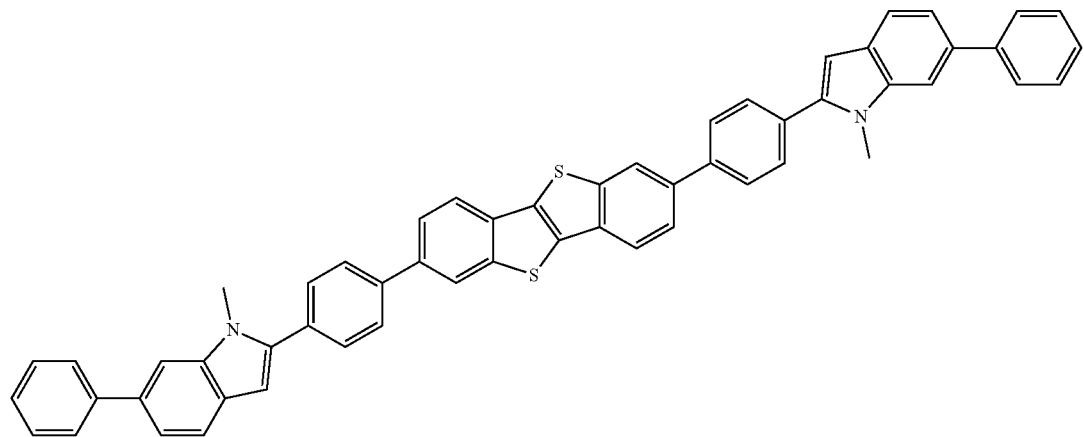
No. 91
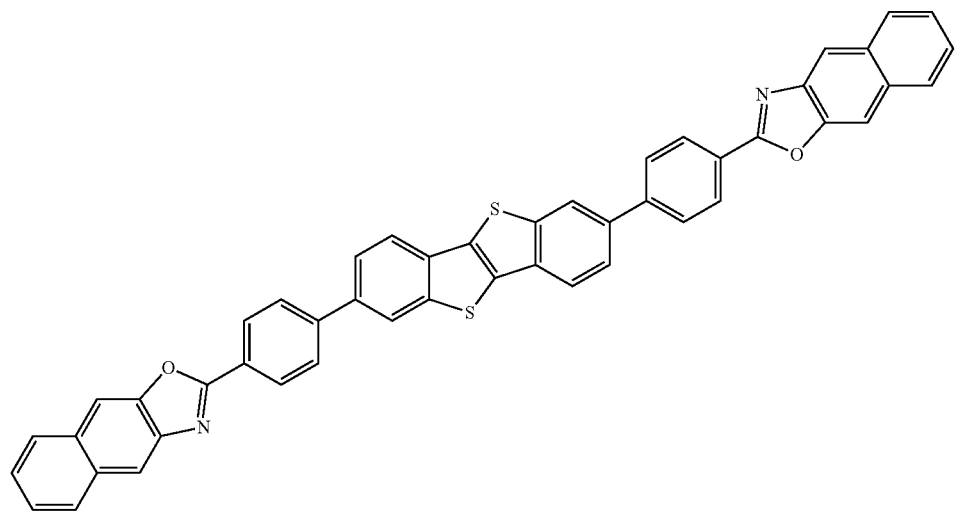

No. 92
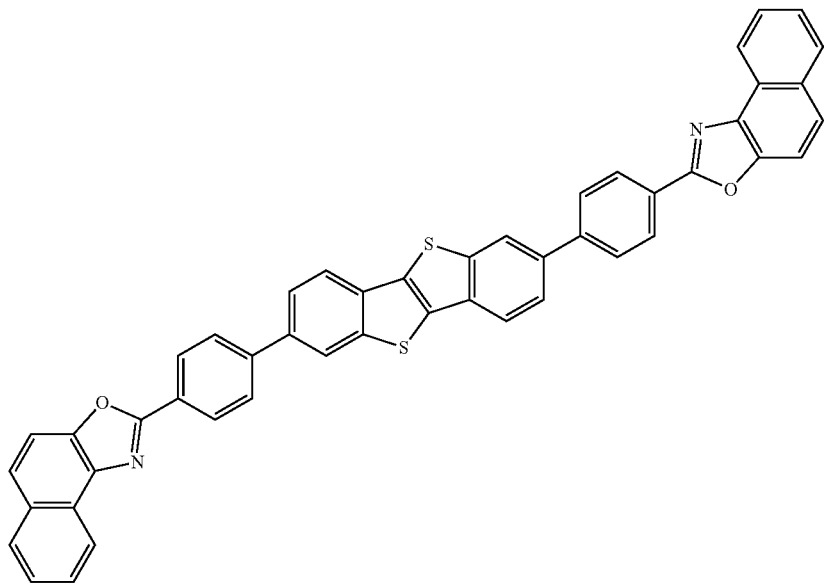
No. 93
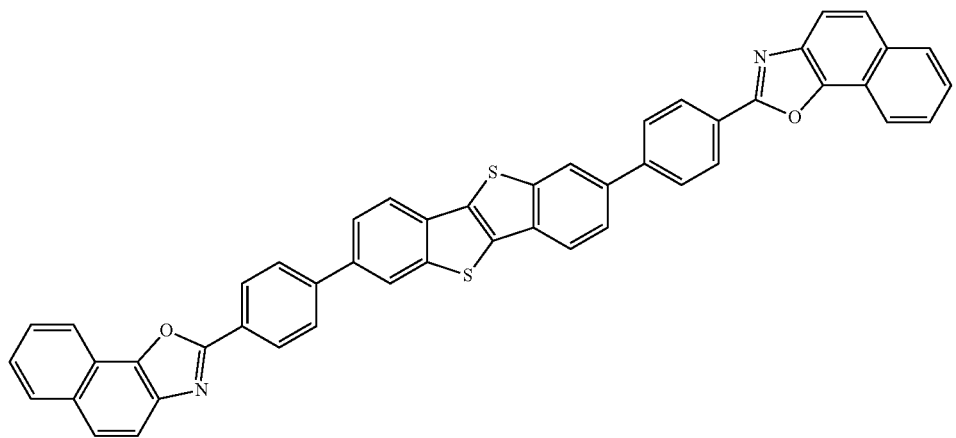
No. 94
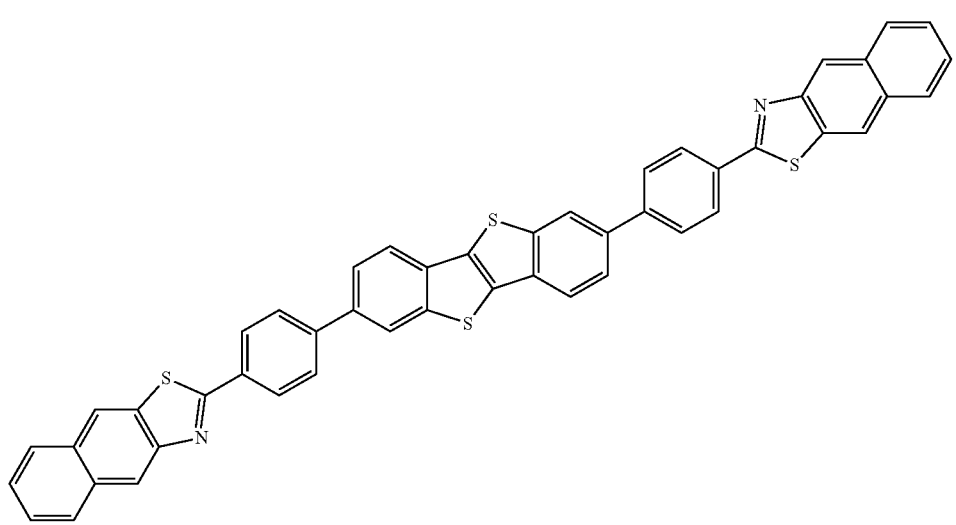

-continued

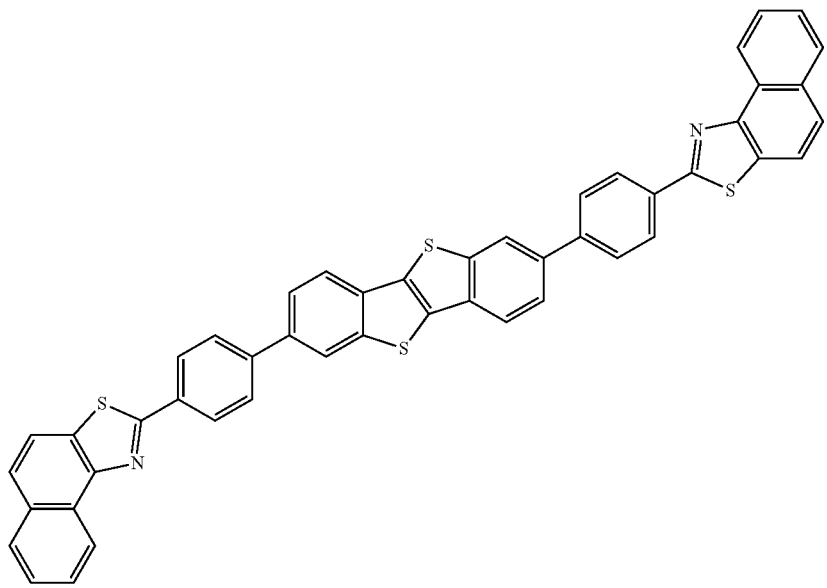

No. 95

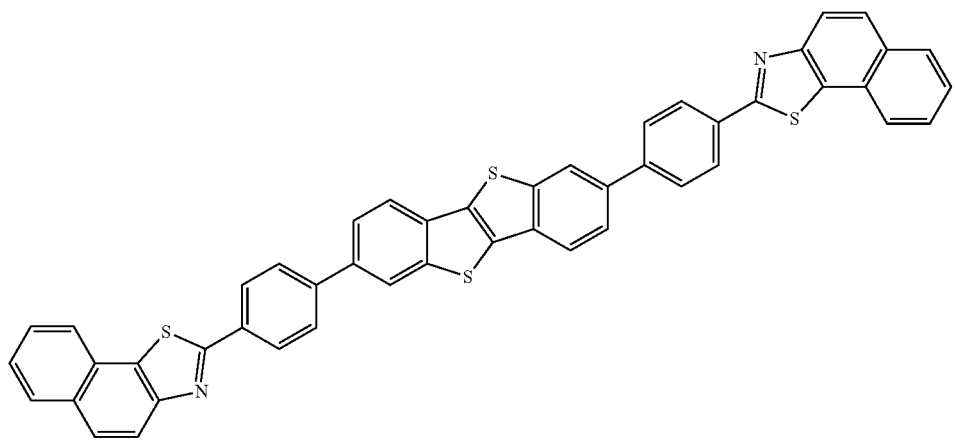

No. 96

The compound represented by the formula (1) can be synthesized by, for example, any of methods known in the art which are disclosed in Patent Literature 1, Patent Literature 6, and Non Patent Literature 1. Examples of such methods include a synthesis method employing the scheme below. A benzothienobenzothiophene skeleton (D) is formed using a nitrostilbene derivative (A) as a starting material and is reduced to produce an aminated form (E). Halogenating the compound (E) provides a halogenated form (F) (the scheme below shows an iodide as an example of the halogen in the halogenated form (F), but this example is not limiting), which then couples with a boric acid derivative to provide the compound represented by the formula (1). The method of Patent Literature 5 is more efficient because the compound represented by the formula (1) can be manufactured in one step from the corresponding benzaldehyde derivative.

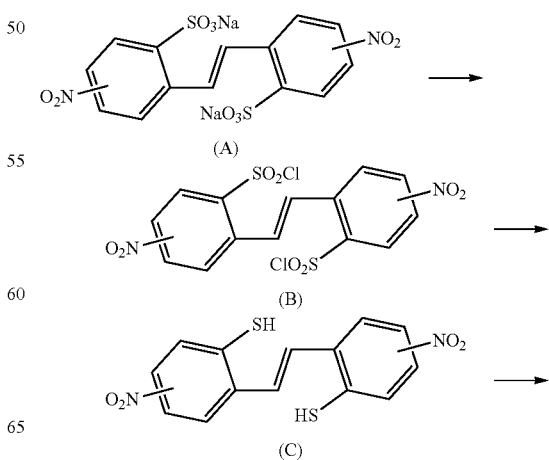

-continued

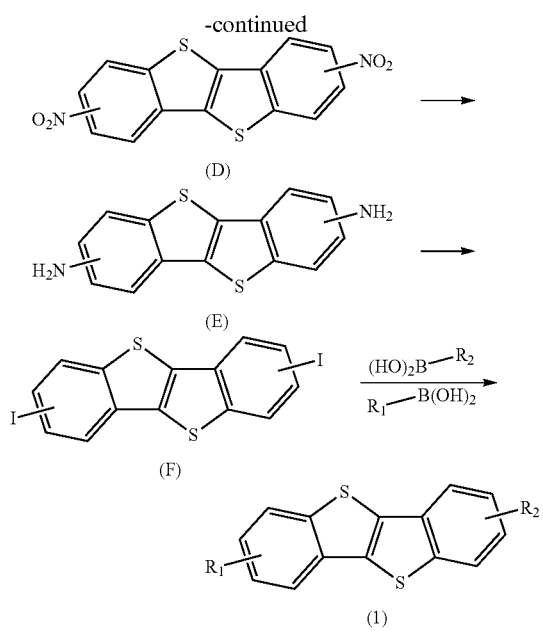

(1)

A method for purifying the compound represented by the formula (1) is not particularly limited, and a method known in the art such as recrystallization, column chromatography, and vacuum sublimation purification can be adopted. If necessary, these methods can be combined.

The photoelectric conversion element for use in an imaging element (hereinafter also simply referred to as the "photoelectric conversion element") of the present invention is an element in which a photoelectric conversion portion (C) is disposed between two electrode films facing each other, i.e., a first electrode film (A) and a second electrode film (B). Light enters the photoelectric conversion portion from above the first electrode film (A) or the second electrode film (B). The photoelectric conversion portion (C) generates electrons and holes according to the incident light intensity. A semiconductor reads a signal responding to the charge, and the element provides the incident light intensity responding to the absorption wavelength of the photoelectric conversion film portion. A transistor for readout may be connected to the electrode film on the side where light does not enter. When a large number of photoelectric conversion elements are arranged in an array, these elements serve as an imaging element because the photoelectric conversion elements provide information on the position of incidence in addition to the incident light intensity. A plurality of photoelectric conversion elements may be laminated for use as long as a photoelectric conversion element positioned closer to a light source does not block (transmits) the absorption wavelength of a photoelectric conversion element disposed therebehind when viewed from the light source side. A multicolor imaging element (full-color photodiode array) can be formed by laminating and using a plurality of photoelectric conversion elements having their distinctive absorption wavelengths in the visible region.

The material for a photoelectric conversion element for use in an imaging element of the present invention is used as a material for a layer constituting the photoelectric conversion portion (C) described above.

The photoelectric conversion portion (C) is often composed of a photoelectric conversion layer (c-1) and one or more organic thin-film layer(s) (c-2) other than the photoelectric conversion layer, selected from the group consisting of an electron transport layer, a hole transport layer, an electron blocking layer, a hole blocking layer, a crystallization prevention layer, and an interlayer contact improvement layer, etc. The material for a photoelectric conversion element for use in an imaging element of the present invention can be used in both of the photoelectric conversion layer (c-1) and the organic thin-film layer (c-2) other than the photoelectric conversion layer and is preferably used in the organic thin-film layer (c-2) other than the photoelectric conversion layer.

When the photoelectric conversion layer (c-1) comprised in the photoelectric conversion portion (C) mentioned later has hole transport properties or when the organic thin-film layer (c-2) other than the photoelectric conversion layer (hereinafter the organic thin-film layer other than the photoelectric conversion layer is also simply referred to as the "organic thin-film layer (c-2)") is a hole transport layer having hole transport properties, the first electrode film (A) and the second electrode film (B) carried by the photoelectric conversion element for use in an imaging element of the present invention play roles in extracting holes from the photoelectric conversion layer (c-1) or the organic thin-film layer (c-2) and collecting the holes. When the photoelectric conversion layer (c-1) comprised in the photoelectric conversion portion (C) has electron transport properties or when the organic thin-film layer (c-2) is an electron transport layer having electron transport properties, the first electrode film (A) and the second electrode film (B) play roles in extracting electrons from the photoelectric conversion layer (c-1) or the organic thin-film layer (c-2) and discharging the electrons. Accordingly, the material that may be used for each of the first electrode film (A) and the second electrode film (B) is not particularly limited as long as the material has conductivity to some extent. The material is preferably selected in consideration of adhesion to the adjacent photoelectric conversion layer (c-1) or organic thin-film layer (c-2), electron affinity, ionization potential, stability, etc. Examples of the material that may be used for each of the first electrode film (A) and the second electrode film (B) include: conductive metal oxides such as tin oxide (NESA), indium oxide, tin-doped indium oxide (ITO), and zinc-doped indium oxide (IZO); metals such as gold, silver, platinum, chromium, aluminum, iron, cobalt, nickel, and tungsten; inorganic conductive substances such as copper iodide and copper sulfide; conductive polymers such as polythiophene, polypyrrole, and polyaniline; and carbon. These materials may be used, if necessary, as a mixture of two or more thereof or as a laminate of two or more layers thereof. The conductivity of the material for use in each of the first electrode film (A) and the second electrode film (B) is not particularly limited unless the conductivity interferes more than necessary with the light reception of the photoelectric conversion element. The conductivity is preferably as high as possible from the viewpoint of the signal intensity and power consumption of the photoelectric conversion element. For example, an ITO film having conductivity with a sheet resistance of 300 Ω/□ or smaller functions adequately as each of the first electrode film (A) and the second electrode film (B). However, a commercially available substrate equipped with an ITO film having conductivity with a sheet resistance on the order of several Ω/□ can also be obtained. Therefore, it is desirable to use such a substrate having high conductivity. The thickness of the ITO film (electrode film) can be arbitrarily selected in consideration of conductivity and is usually on the order of 5 to 500 nm, preferably 10 to 300 nm. Examples of methods for forming the film such as ITO include vapor deposition methods, electron beam methods, sputtering methods, chemical reaction methods, and coating methods conventionally known in the art. If necessary, the ITO film disposed on the substrate may be subjected to UV-ozone treatment, plasma treatment, or the like.

Examples of the material for the transparent electrode film that is used as at least one (electrode film on the side where light enters) of the first electrode film (A) and the second electrode film (B) include ITO, IZO, $SnO_2$, ATO (antimony-doped tin oxide), ZnO, AZO (Al-doped zinc oxide), GZO (gallium-doped zinc oxide), $TiO_2$, and FTO (fluorine-doped tin oxide). The transmittance of the incident light via the transparent electrode film is preferably 60% or higher, more preferably 80% or higher, particularly preferably 95% or higher, at the absorption peak wavelength of the photoelectric conversion layer (c-1).

In the case of laminating a plurality of photoelectric conversion layers differing in wavelengths to be detected, an electrode film (which is an electrode film other than the first electrode film (A) and the second electrode film (B)) for use between the photoelectric conversion layers needs to transmit light having wavelengths other than the light to be detected by each photoelectric conversion layer. For this electrode film, it is preferred to use a material that transmits 90% or more of the incident light, and it is more preferred to use a material that transmits 95% or more of the light.

The electrode films are preferably prepared by a plasma-free method. Preparing these electrode films by a plasma-free method can reduce the influence of plasma on the substrate provided with the electrode films and improve the photoelectric conversion characteristics of the photoelectric conversion element. In this context, the term "plasma-free" means that, during the formation of the electrode films, no plasma is generated or the distance from a plasma source to the substrate is 2 cm or more, preferably 10 cm or more, more preferably 20 cm or more, such that the plasma arriving at the substrate is decreased.

Examples of apparatuses that generate no plasma during the formation of the electrode films include electron beam vapor deposition apparatuses (EB vapor deposition apparatuses) and pulse laser vapor deposition apparatuses. Hereinafter, a film formation method for a transparent electrode film using an EB vapor deposition apparatus is referred to as an EB vapor deposition method, and a film formation method for a transparent electrode film using a pulse laser vapor deposition apparatus is referred to as a pulse laser vapor deposition method.

For example, a facing target sputtering apparatus or an arc plasma vapor deposition apparatus is possible as an apparatus that can achieve a state where plasma can be decreased during the film formation (hereinafter referred to as a plasma-free film formation apparatus).

In the case of using a transparent conductive film as an electrode film (e.g., a first conductive film), DC short or increase in leakage current may occur. A possible cause thereof is that fine cracks generated in the photoelectric conversion layer are covered with a compact film such as TCO (transparent conductive oxide) to increase continuity with an electrode film (second conductive film) on a side opposite to the transparent conductive film. Therefore, in the case of using a material, such as Al, which has relatively poor film quality in an electrode, increase in leakage current is less likely to occur. The increase in leakage current can be suppressed by controlling the film thickness of each electrode film according to the film thickness (depth of cracks) of the photoelectric conversion layer.

In general, when the conductive film is thinner than a predetermined value, sharp increase in resistance occurs.

The sheet resistance of the conductive film in the photoelectric conversion element for use in an imaging element of the present embodiment is usually 100 to 10000 Ω/□ at which the degree of freedom of the film thickness is large. A thinner transparent conductive film absorbs a smaller amount of light and generally has a higher light transmittance. Such a higher light transmittance is very preferred because the light absorbed by the photoelectric conversion layer is increased to improve the photoelectric conversion ability.

The photoelectric conversion portion (C) carried by the photoelectric conversion element for use in an imaging element of the present invention comprises at least the photoelectric conversion layer (c-1) and the organic thin-film layer (c-2) other than the photoelectric conversion layer.

In general, an organic semiconductor film is used as the photoelectric conversion layer (c-1) constituting the photoelectric conversion portion (C). The organic semiconductor film may be one layer or a plurality of layers. For one layer, a p-type organic semiconductor film, an n-type organic semiconductor film, or a mixed film thereof (bulk heterostructure) is used. On the other hand, the plurality of layers are generally on the order of 2 to 10 layers and have a structure having a laminate of p-type organic semiconductor films, n-type organic semiconductor films, or mixed films thereof (bulk heterostructure). A buffer layer may be inserted between the layers.

A triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a carbazole derivative, a naphthalene derivative, an anthracene derivative, a chrysene derivative, a phenanthrene derivative, a pentacene derivative, a phenylbutadiene derivative, a styryl derivative, a quinoline derivative, a tetracene derivative, a pyrene derivative, a perylene derivative, a fluoranthene derivative, a quinacridone derivative, a coumarin derivative, a porphyrin derivative, a fullerene derivative, a metal complex (Ir complex, Pt complex, Eu complex, etc.), or the like can be used in the organic semiconductor film of the photoelectric conversion layer (c-1) according to the wavelength band to be absorbed.

In the photoelectric conversion element for use in an imaging element of the present invention, the organic thin-film layer (c-2) other than the photoelectric conversion layer constituting the photoelectric conversion portion (C) is also used as a layer other than the photoelectric conversion layer (c-1), for example, an electron transport layer, a hole transport layer, an electron blocking layer, a hole blocking layer, a crystallization prevention layer, or an interlayer contact improvement layer. It is particularly preferred to use the organic thin-film layer (c-2) as one or more thin-film layer(s) selected from the group consisting of an electron transport layer, a hole transport layer, an electron blocking layer, and a hole blocking layer because the resulting element efficiently converts even weak light energy to an electric signal.

The electron transport layer plays roles in transporting electrons generated in the photoelectric conversion layer (c-1) to the first electrode film (A) or the second electrode film (B) and blocking the transfer of holes from the electrode film as an electron acceptor to the photoelectric conversion layer (c-1).

The hole transport layer plays roles in transporting generated holes from the photoelectric conversion layer (c-1) to the first electrode film (A) or the second electrode film (B) and blocking the transfer of electrons from the electrode film as a hole acceptor to the photoelectric conversion layer (c-1).

The electron blocking layer plays roles in blocking the transfer of electrons from the first electrode film (A) or the second electrode film (B) to the photoelectric conversion layer (c-1), preventing recombination in the photoelectric conversion layer (c-1), and reducing dark current.

The hole blocking layer has the functions of blocking the transfer of holes from the first electrode film (A) or the second electrode film (B) to the photoelectric conversion layer (c-1), preventing recombination in the photoelectric conversion layer (c-1), and reducing dark current.

The hole blocking layer is formed by using a substance capable of blocking holes alone or by laminating or mixing two or more of substances capable of blocking holes. The substance capable of blocking holes is not limited as long as the substance is a compound that can prevent the efflux of the holes from the electrode to the outside of the element. Examples of the compound that can be used in the hole blocking layer include the compound represented by the general formula (1) described above as well as phenanthroline derivatives such as bathophenanthroline and bathocuproine, silole derivatives, quinolinol derivative-metal complexes, oxadiazole derivatives, oxazole derivatives, and quinoline derivatives. One or two or more of these compounds can be used.

The organic thin-film layer (c-2) other than the photoelectric conversion layer comprises the compound represented by the general formula (1) described above and can be suitably used particularly as a hole blocking layer. A larger film thickness of the hole blocking layer is more preferred from the viewpoint of preventing leakage current. A film thickness is more preferably as small as possible from the viewpoint of obtaining a sufficient amount of current for signal readout at the time of light incidence. For achieving these conflicting characteristics, it is generally preferred that the photoelectric conversion portion (C) comprising the photoelectric conversion layer (c-1) and the organic thin-film layer (c-2) other than the photoelectric conversion layer should have a film thickness on the order of 5 to 500 nm. How the layer comprising the compound represented by the general formula (1) works varies depending on the other compounds used in the photoelectric conversion element.

For avoiding interference with the light absorption of the photoelectric conversion layer (c-1), it is preferred that the hole blocking layer and the electron blocking layer should have a high transmittance at the absorption wavelength of the photoelectric conversion layer and should be used as thin films.

A thin-film transistor outputs a signal to a signal readout portion on the basis of the charge generated by the photoelectric conversion portion. The thin-film transistor includes a gate electrode, a gate insulator film, an active layer, a source electrode, and a drain electrode. The active layer is formed of a silicon semiconductor, an oxide semiconductor, or an organic semiconductor.

When the active layer for use in the thin-film transistor is formed of an oxide semiconductor, its charge mobility is far higher than that of an active layer formed of amorphous silicon, and operation at low voltage is achieved. In addition, a flexible active layer that usually has a higher light transmittance than in the case of silicon can be formed using an oxide semiconductor. An oxide semiconductor, particularly an amorphous oxide semiconductor, is particularly advantageous when a flexible resin substrate such as plastics is used because a film of the semiconductor of uniform thickness can be formed at low temperatures (e.g., room temperature). In addition, when a plurality of secondary light receiving pixels are laminated, formation of secondary light receiving pixels on the upper side affects secondary light receiving pixels on the lower side. In particular, the photoelectric conversion layer is apt to be affected by heat. Oxide semiconductors, particularly amorphous oxide semiconductors, are advantageous because a film of such a semiconductor can be formed at low temperatures.

An oxide semiconductor used to form the active layer is preferably an oxide (such as In—O) containing at least one of In, Ga, and Zn, more preferably an oxide (such as In—Zn—O, In—Ga—O, and Ga—Zn—O) containing at least two of In, Ga, and Zn, further preferably an oxide containing In, Ga, and Zn. The In—Ga—Zn—O-based oxide semiconductor is preferably an oxide semiconductor represented by $InGaO_3(ZnO)_m$ (where m is a natural number less than 6) in terms of the composition in the crystalline state, particularly preferably $InGaZnO_4$. A feature of the amorphous oxide semiconductor of this composition is that its electron mobility is likely to increase as the electric conductivity increases.

The signal readout portion reads charge generated and accumulated in the photoelectric conversion portion or a voltage responding to the charge.

FIG. 1 illustrates the details of a typical element structure of the photoelectric conversion element for use in an imaging element of the present invention. However, the present invention is not intended to be limited by this structure. In the exemplary embodiment of FIG. 1, reference numeral 1 denotes an insulation portion, reference numeral 2 denotes one of the electrode films (upper electrode; that is, first electrode film or second electrode film), reference numeral 3 denotes an electron blocking layer (or hole transport layer), reference numeral 4 denotes a photoelectric conversion layer, reference numeral 5 denotes a hole blocking layer (or electron transport layer), reference numeral 6 denotes the other electrode film (lower electrode; that is, second electrode film or first electrode film), and reference numeral 7 denotes an insulating base material or another photoelectric conversion element. A readout transistor (not shown in the drawing) can be connected to either the electrode film 2 or the electrode 6. For example, provided that the photoelectric conversion layer 4 is transparent, this film may be formed on the outside (i.e., the upside of the electrode film 2 or the downside of the electrode film 6) of the electrode film on a side opposite to the side where light enters. Provided that a thin-film layer (electron blocking layer, hole blocking layer, etc.) other than the photoelectric conversion layer constituting the photoelectric conversion element does not extremely mask the absorption wavelength of the photoelectric conversion layer, the incident direction of light can be any of the upward direction (incidence from the insulation portion 1 side in FIG. 1) or the downward direction (incidence from the insulating substrate 7 side in FIG. 1).

In general, for example, a vacuum process (resistance heating vacuum vapor deposition, electron beam vapor deposition, sputtering, and molecular lamination), a solution process (coating methods such as casting, spin coating, dip coating, blade coating, wire bar coating, and spray coating; printing methods such as inkjet printing, screen printing, offset printing, and relief printing; and soft lithography approaches such as microcontact printing), or a method using a combination of two or more of these approaches can be adopted as a method for forming the photoelectric conversion layer (c-1) and the organic thin-film layer (c-2) other than the photoelectric conversion layer in the photoelectric conversion element for use in an imaging element of the present invention. The thickness of each layer also depends on the resistance and charge mobility of each substance and thus cannot be limited. The thickness of each layer is usually in the range of 1 to 5000 nm, preferably in the range of 3 to 1000 nm, more preferably in the range of 5 to 500 nm.

EXAMPLES

Hereinafter, the present invention will be described in more detail with reference to Examples, but the present invention is not limited to these examples. In the Examples, parts represent parts by mass unless otherwise specified, and % represents percent by mass.

The blocking layer described in Examples can be any of the hole blocking layer and the electron blocking layer. The photoelectric conversion element was prepared in a vapor deposition machine integrated with a glove box, and the prepared photoelectric conversion element was placed in a hermetically sealable bottle-shaped measurement chamber (manufactured by ALS Technology Co., Ltd.) in the glove box having a nitrogen atmosphere, and subjected to the application and measurement of current and voltage. The application and measurement of the current and voltage were conducted using a semiconductor parameter analyzer 4200-SCS (Keithley Instruments, Inc.), unless otherwise specified. Irradiation with incident light was carried out at a light wavelength of 550 nm and a light half-value width of 20 nm using PVL-3300 (manufactured by Asahi Spectra Co., Ltd.), unless otherwise specified. In Examples, a light-dark ratio represents a value determined by dividing a current value in the case of light irradiation by a current value in the dark.

Synthesis Example 1

Synthesis of 2,7-bis(4-(benzo[b]furan-2-yl) phenyl)[1] benzothieno[3,2-b][1] benzothiophene (Compound Represented by No. 1 in the Specific Examples))

Step 1 (Synthesis of 2-(4-bromophenyl) benzo[b]furan)

To DMF (920 parts), benzo[b]furan-2-ylboronic acid (14.8 parts), which is generally available, para-bromoiodobenzene (25.8 parts), tripotassium phosphate (110 parts) and tetrakis(triphenylphosphine) palladium (2.8 parts) were mixed, and the mixture was stirred at 90° C. for 6 hours, under a nitrogen atmosphere. The obtained reaction liquid was cooled to room temperature. Then, water (920 parts) was added thereto, and the solid matter was collected by filtration. The obtained solid matter was washed with methanol, and dried to obtain 2-(4-bromophenyl)benzo[b]furan (6.6 parts and yield of 26%).

Step 2 (Synthesis of 2-(4-(benzo[b]furan-2-yl)phenyl)-4,4,5,5-tetramethyl-1,3,2-dioxaborolane)

To toluene (240 parts), 2-(4-bromophenyl)benzo[b]furan (5.0 parts), which was obtained in the step 1, bis(pinacolato) diboron (5.6 parts), potassium acetate (3.5 parts) and a [1,1'-bis(diphenylphosphino)ferrocene]palladium(II)dichloride dichloromethane adduct (0.5 parts) were mixed, and the mixture was stirred at a reflux temperature for 4 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(4-(benzo [b]furan-2-yl)phenyl)-4,4,5,5-tetramethyl-1,3,2-dioxaborolane (5.2 parts and yield of 88%).

Step 3 (Synthesis of 2,7-bis(4-(benzo[b]furan-2-yl) phenyl)[1]benzothieno[3,2-b][1]benzothiophene)

To DMF (200 parts), water (6.0 parts), 2,7-diiodo[1] benzothieno[3,2-b][1]benzothiophene (3.0 parts), which was synthesized according to the method described in Japanese Patent No. 4945757, 2-(4-(benzo[b]furan-2-yl)phenyl)-4,4,5,5-tetramethyl-1,3,2-dioxaborolane (5.0 parts), which was obtained in the step 2, tripotassium phosphate (20 parts) and tetrakis (triphenylphosphine)palladium (0.4 parts) were mixed, and the mixture was stirred at 90° C. for 6 hours, under a nitrogen atmosphere. The obtained reaction liquid was cooled to room temperature. Then, water (200 parts) was added thereto, and the solid matter was collected by filtration. The obtained solid matter was washed with acetone, dried, and then purified by sublimation to obtain a compound (2.0 parts and yield of 50%) represented by No. 1 in the specific examples described above.

Synthesis Example 2

Synthesis of 2,7-bis(4-(benzo[b]thiophen-2-yl)phenyl)[1]benzothieno[3,2-b][1]benzothiophene (Compound Represented by No. 5 in the Specific Examples Step 4 (Synthesis of 2-(4-bromophenyl) benzo[b]thiophene)

To DMF (300 parts), benzo[b]thiophen-2-ylboronic acid (5.0 parts), which is generally available, para-bromoiodobenzene (7.9 parts), tripotassium phosphate (34 parts) and tetrakis(triphenylphosphine) palladium (0.84 parts) were mixed, and the mixture was stirred at 90° C. for 6 hours, under a nitrogen atmosphere. The obtained reaction liquid was cooled to room temperature. Then, water (300 parts) was added thereto, and the solid matter was collected by filtration. The obtained solid matter was washed with methanol, and dried to obtain 2-(4-bromophenyl)benzo[b]thiophene (5.7 parts and yield of 70%).

Step 5 (Synthesis of 2-(4-(benzo[b]thiophen-2-yl) phenyl)-4,4,5,5-tetramethyl-1,3,2-dioxaborolane)

To toluene (240 parts), 2-(4-bromophenyl)benzo[b]thiophene (5.3 parts), which was obtained in the step 4, bis (pinacolato)diboron (5.6 parts), potassium acetate (3.5 parts) and a [1,1'-bis(diphenylphosphino)ferrocene]palladium(II) dichloride dichloromethane adduct (0.5 parts) were mixed, and the mixture was stirred at a reflux temperature for 4 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(4-(benzo [b]thiophen-2-yl)phenyl)-4,4,5,5-tetramethyl-1,3,2-dioxaborolane (4.5 parts and yield of 73%).

Step 6 (Synthesis of 2,7-bis(4-(benzo[b]thiophen-2-yl)phenyl)[1]benzothieno[3,2-b][1]benzothiophene)

To DMF (170 parts), water (5.0 parts), 2,7-diiodo[1]benzothieno[3,2-b][1]benzothiophene (2.6 parts), which was synthesized according to the method described in Japanese Patent No. 4945757, 2-(4-(benzo[b]thiophen-2-yl)phenyl)-4,4,5,5-tetramethyl-1,3,2-dioxaborolane (4.5 parts), which was obtained in the step 5, tripotassium phosphate (18 parts) and tetrakis (triphenylphosphine)palladium (0.35 parts) were mixed, and the mixture was stirred at 90° C. for 6 hours, under a nitrogen atmosphere. The obtained reaction liquid was cooled to room temperature. Then, water (170 parts) was added thereto, and the solid matter was collected by filtration. The obtained solid matter was washed with acetone, dried, and then purified by sublimation to obtain a compound (1.6 parts and yield of 46%) represented by No. 5 in the specific examples described above.

Synthesis Example 3

Synthesis of 2,7-bis(4-(benzo[d]thiazol-2-yl)phenyl)[1]benzothieno[3,2-b][1]benzothiophene (Compound Represented by No. 29 in the Specific Examples))

Step 7 (Synthesis of 2-(4-(4,4,5,5-tetramethyl-1,3,2-dioxaborolan-2-yl)phenyl)benzo[d]thiazole)

To toluene (240 parts), 2-(4-bromophenyl)benzo[d] thiazole (5.3 parts), which is generally available, bis(pinacolato)diboron (5.6 parts), potassium acetate (3.5 parts) and a [1,1'-bis(diphenylphosphino)ferrocene]palladium(II)dichloride dichloromethane adduct (0.5 parts) were mixed, and the mixture was stirred at a reflux temperature for 4 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(4-(4,4,5,5-tetramethyl-1,3,2-dioxaborane-2-yl)phenyl)benzo[d]thiazole (4.9 parts and yield of 80%).

Step 8 (Synthesis of 2,7-bis(4-(benzo[d]thiazol-2-yl)phenyl)[1]benzothieno[3,2-b][1]benzothiophene)

To DMF (170 parts), water (5.0 parts), 2,7-diiodo[1]benzothieno[3,2-b][1]benzothiophene (2.6 parts), which was synthesized according to the method described in Japanese Patent No. 4945757, 2-(4-(4,4,5,5-tetramethyl-1,3,2-dioxaborane-2-yl)phenyl)benzo[d]thiazole (4.5 parts), which was obtained in the step 7, tripotassium phosphate (18 parts) and tetrakis(triphenylphosphine)palladium (0.35 parts) were mixed, and the mixture was stirred at 90° C. for 6 hours under a nitrogen atmosphere. The obtained reaction liquid was cooled to room temperature. Then, water (170 parts) was added thereto, and the solid matter was collected by filtration. The obtained solid matter was washed with acetone, dried, and then purified by sublimation to obtain a compound (1.8 parts and yield of 52%) represented by No. 29 in the specific examples described above.

Synthesis Example 4

Synthesis of 2,7-bis(4-(5-benzo[b]thienyl)phenyl)[1]benzothieno[3,2-b][1]benzothiophene Step 9 (synthesis of 2-(benzo[b]thiophen-5-yl)-4,4,5,5-tetramethyl-1,3,2-dioxaborolane)

To toluene (200 parts), 5-bromobenzo[b]thiophene (10.0 parts), bis(pinacolato)diboron (14.3 parts), potassium acetate (9.2 parts) and a [1,1'-bis(diphenylphosphino)ferrocene]palladium(II)dichloride dichloromethane adduct (1.1 parts) were mixed, and the mixture was stirred at a reflux temperature for 2 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene), and the solvent was removed under reduced pressure to obtain 2-(benzo[b]thiophen-5-yl)-4,4,5,5-tetramethyl-1,3,2-dioxaborolane (11.7 parts and yield of 96%).

Step 10 (Synthesis of 5-(4-bromophenyl)benzo[b]thiophene)

To DMF (230 parts), 2-(benzo[b]thiophen-5-yl)-4,4,5,5-tetramethyl-1,3,2-dioxaborolane (11.5 parts), which was obtained in the step 9, 1-bromo-4-iodobenzene (12.5 parts), tripotassium phosphate (18.7 parts) and tetrakis(triphenylphosphine)palladium (1.6 parts) were mixed, and the mixture was stirred at 60° C. for 2 hours, under a nitrogen atmosphere. The obtained reaction liquid was cooled to room temperature. Then, water (200 parts) was added thereto, and the solid matter was collected by filtration. The obtained solid matter was washed with water and methanol in this order to obtain 5-(4-bromophenyl)benzo[b]thiophene (12.0 parts and yield of 94%).

Step 11 (Synthesis of 2-(4-(5-benzo[b]thienyl)phenyl)-4,4,5,5-tetramethyl-1,3,2-dioxaborolane)

To toluene (200 parts), 5-(4-bromophenyl)benzo[b]thiophene (12.0 parts), which was obtained in the step 10, bis(pinacolato) diboron (14.5 parts), potassium acetate (9.3 parts) and a [1,1'-bis(diphenylphosphino)ferrocene]palladium(II)dichloride dichloromethane adduct (1.2 parts) were mixed, and the mixture was stirred at a reflux temperature for 4 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene), and the solvent was removed under reduced pressure. The obtained pale orange solid was washed with methanol to obtain 2-(4-(5-benzo[b]thienyl)phenyl)-4,4,5,5-tetramethyl-1,3,2-dioxaborolane (7.4 parts and yield of 53%).

Step 12 (Synthesis of 2,7-bis(4-(5-benzo[b]thienyl)phenyl)[1]benzothieno[3,2-b][1]benzothiophene)

To DMF (200 parts), water (10.0 parts), 2,7-diiodo[1]benzothieno[3,2-b][1]benzothiophene (3.7 parts), which was synthesized according to the method described in Japanese Patent No. 4945757, and 2-(4-(5-benzo[b]thienyl)phenyl)-4,4,5,5-tetramethyl-1,3,2-dioxaborolane (6.3 parts), which was obtained in the step 11, tripotassium phosphate (6.4 parts) and tetrakis(triphenylphosphine)palladium (0.5 parts) were mixed, and the mixture was stirred at 80° C. for 6 hours, under a nitrogen atmosphere. The obtained reaction liquid was cooled to room temperature. Then, water (150 parts) was added thereto, and the solid matter was collected by filtration. The obtained solid matter was washed with acetone and DMF, dried, and then purified by sublimation to obtain the objective compound (2.0 parts and yield of 51%).

Synthesis Example 5 (Synthesis of 2,7-bis(4-(naphtho[1,2-b]thiophen-2-yl)phenyl)[1]benzothieno[3,2-b][1]benzothiophene (Compound Represented by No. 69 in the Specific Examples))

Step 13 (synthesis of 2-(4-bromophenyl)naphtho[1,2-b]thiophene)

To DMF (190 parts), 2-(naphtho[1,2-b]thiophen-2-yl)-4,4,5,5-tetramethyl-1,3,2-dioxaborolane (6.0 parts), which was synthesized by a known method, para-bromoiodobenzene (5.5 parts), water (5.0 parts), tripotassium phosphate (22.9 parts) and tetrakis(triphenylphosphine)palladium (0.6 parts) were mixed, and the mixture was stirred at 70° C. for 4 hours, under a nitrogen atmosphere. The obtained reaction liquid was cooled to room temperature. Then, water (190 parts) was added thereto, and the solid matter was collected by filtration. The obtained solid matter was washed with methanol, and dried to obtain 2-(4-bromophenyl)naphtho[1,2-b]thiophene (3.0 parts and yield of 47%).

Step 14 (Synthesis of 2-(4-(naphtho[1,2-b]thiophen-2-yl)phenyl)-4,4,5,5-tetramethyl-1,3,2-dioxaborolane)

To toluene (110 parts), 2-(4-bromophenyl)naphtho[1,2-b]thiophene (2.8 parts), which was obtained in the step 13, bis(pinacolato)diboron (2.5 parts), potassium acetate (1.6 parts) and a [1,1'-bis(diphenylphosphino)ferrocene]palladium(II) dichloride dichloromethane adduct (0.22 parts) were mixed, and the mixture was stirred at a reflux temperature for 4 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(4-(naphtho[1,2-b]thiophen-2-yl)phenyl)-4,4,5,5-tetramethyl-1,3,2-dioxaborolane (2.2 parts and yield of 69%).

Step 15 (synthesis of 2,7-bis(4-(naphtho[1,2-b]thiophen-2-yl)phenyl)[1]benzothieno[3,2-b][1]benzothiophene)

To DMF (100 parts), water (2.6 parts), 2,7-diiodo[1]benzothieno[3,2-b][1]benzothiophene (1.2 parts), which was synthesized according to the method described in Japanese Patent No. 4945757, 2-(4-(naphtho[1,2-b]thiophen-2-yl)phenyl)-4,4,5,5-tetramethyl-1,3,2-dioxaborolane (2.0 parts), which was obtained in the step 14, tripotassium phosphate (8.1 parts) and tetrakis(triphenylphosphine)palladium (0.2 parts) were mixed, and the mixture was stirred at 80° C. for 5 hours, under a nitrogen atmosphere. The obtained reaction liquid was cooled to room temperature. Then, water (100 parts) was added thereto, and the solid matter was collected by filtration. The obtained solid matter was washed with acetone, dried, and then purified by sublimation to obtain a compound (0.4 parts and yield of 26%) represented by No. 69 in the specific examples described above.

Synthesis Example 6

Synthesis of 2,7-bis(4-(naphtho[2,3-b]thiophen-2-yl)phenyl)[1]benzothieno[3,2-b][1]benzothiophene (Compound Represented by No. 20 in the Specific Examples))

Step 16 (Synthesis of 2-(4-bromophenyl)naphtho[2,3-b]thiophene)

2-(4-Bromophenyl)naphtho[2,3-b]thiophene (3.5 parts and yield of 55%) was obtained by performing synthesis according to the step 13, except that in place of 2-(naphtho[1,2-b]thiophen-2-yl)-4,4,5,5-tetramethyl-1,3,2-dioxaborolane, 2-(naphtho[2,3-b]thiophen-2-yl)-4,4,5,5-tetramethyl-1,3,2-dioxaborolane was used which was synthesized by a known method.

Step 17 (Synthesis of 2-(4-(naphtho[2,3-b]thiophen-2-yl)phenyl)-4,4,5,5-tetramethyl-1,3,2-dioxaborolane)

2-(4-(Naphtho[2,3-b]thiophen-2-yl)phenyl)-4,4,5,5-tetramethyl-1,3,2-dioxaborolane (3.7 parts and yield of 58%) was obtained by performing synthesis according to the step 14, except that in place of 2-(4-bromophenyl)naphtho[1,2-b]thiophene, 2-(4-bromophenyl)naphtho[2,3-b]thiophene was used which was obtained in the step 16.

Step 18 (Synthesis of 2,7-bis(4-(naphtho[2,3-b]thiophen-2-yl)phenyl)[1]benzothieno[3,2-b][1]benzothiophene)

A compound (0.6 parts and yield of 39%) represented by No. in the specific examples described above was obtained by performing synthesis according to the step 15, except that in place of 2-(4-(naphtho[1,2-b]thiophen-2-yl) phenyl)-4,4,5,5-tetramethyl-1,3,2-dioxaborolane, 2-(4-(naphtho[2,3-b]thiophen-2-yl)phenyl)-4,4,5,5-tetramethyl-1,3,2-dioxaborolane was used which was obtained in the step 17.

Synthesis Example 7

Synthesis of 2,7-bis(4-(benzo[d]oxazol-2-yl)phenyl)[1]benzothieno[3,2-b][1]benzothiophene (compound represented by No. 30 in the specific examples))

Step 19 (Synthesis of 2-(benzo[d]oxazol-2-yl)phenyl)-4,4,5,5-tetramethyl-1,3,2-dioxaborolane)

To toluene (500 parts), 2-(4-bromophenyl)benzo[d]oxazole (10 parts), bis(pinacolato)diboron (10.8 parts), potassium acetate (6.9 parts) and a [1,1'-bis(diphenylphosphino)ferrocene]palladium (II)dichloride dichloromethane adduct (1.0 part) were mixed, and the mixture was stirred at a reflux temperature for 4 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(benzo[d]oxazol-2-yl)phenyl)-4,4,5,5-tetramethyl-1,3,2-dioxaborolane (11.4 parts and yield of 99%).

Step 20 (synthesis of 2,7-bis(4-(benzo[d]oxazol-2-yl)phenyl)[1]benzothieno[3,2-b][1]benzothiophene)

To DMF (430 parts), water (11 parts), 2,7-diiodo[1]benzothieno[3,2-b][1]benzothiophene (4.9 parts), which was synthesized according to the method described in Japanese Patent No. 4945757), 2-(benzo[d]oxazol-2-yl)phenyl)-4,4,5,5-tetramethyl-1,3,2-dioxaborolane (8.0 parts), which was obtained in the step 19, tripotassium phosphate (34 parts) and tetrakis(triphenylphosphine)palladium (0.8 parts) were mixed, and the mixture was stirred at 80° C. for 5 hours, under a nitrogen atmosphere. The obtained reaction liquid was cooled to room temperature. Then, water (430 parts) was added thereto, and the solid matter was collected by filtration. The obtained solid matter was washed with acetone, dried, and then purified by sublimation to obtain a compound (3.6 parts and yield of 57%) represented by No. 30 in the specific examples described above.

Synthesis Example 8

Synthesis of 2,7-bis(4-(5-phenylbenzo[b]thiophen-2-yl)phenyl)[1]benzothieno[3,2-b][1]benzothiophene (Compound Represented by No. 83 in the Specific Examples))

Step 21 (Synthesis of 5-phenylbenzo[b]thiophene)

To DMF (500 parts), 5-bromobenzo[b]thiophene (20 parts), phenylboronic acid (13.7 parts), tripotassium phosphate (113 parts) and tetrakis(triphenylphosphine)palladium (3.0 parts) were mixed, and the mixture was stirred at 70° C. for 6 hours, under a nitrogen atmosphere. The obtained reaction liquid was cooled to room temperature. Then, water (500 parts) was added thereto, and the solid matter was collected by filtration. The obtained solid matter was washed with water and acetone, and dried to obtain 5-phenylbenzo[b]thiophene (13.3 parts and yield of 67%).

Step 22 (Synthesis of 2-(5-phenylbenzo[b]thiophen-2-yl)-4,4,5,5-tetramethyl-1,3,2-dioxaborolane)

To tetrahydrofuran (300 parts), 5-phenylbenzo[b]thiophene (12.6 parts) was mixed, which was obtained in the step 21. An n-butyllithium hexane solution (2.6 M and 28 parts) was added to the mixed solution which was cooled to 0° C., and the mixture was stirred for 1 hour, under a nitrogen atmosphere. Isopropoxyboronic acid pinacol (16 parts) was added to the obtained mixed solution, and the mixture was stirred at room temperature for 12 hours. Water (100 parts) was added to the obtained reaction liquid, and the solid matter which was formed by distillation from the solvent under reduced pressure was collected by filtration. The obtained solid matter was washed with water, and dried to obtain 2-(5-phenylbenzo[b]thiophen-2-yl)-4,4,5,5-tetramethyl-1,3,2-dioxaborolane (11.4 parts and yield of 57%).

Step 23 (Synthesis of 2-(4-bromophenyl)-5-phenyl-benzo[b]thiophene)

To DMF (300 parts), water (8.0 parts), 2-(5-phenylbenzo[b]thiophen-2-yl)-4,4,5,5-tetramethyl-1,3,2-dioxaborolane (10 parts), which was obtained in the step 22, 1-bromo-4-iodobenzene (8.4 parts), tripotassium phosphate (36 parts) and tetrakis(triphenylphosphine)palladium (1.0 part) were mixed, and the mixture was stirred at 70° C. for 3 hours, under a nitrogen atmosphere. The obtained reaction liquid was cooled to room temperature. Then, water (300 parts) was added thereto, and the solid matter was collected by filtration. The obtained solid matter was washed with water and methanol in this order to obtain 2-(4-bromophenyl)-5-phenylbenzo[b]thiophene (9.2 parts and yield of 85%).

Step 24 (Synthesis of 2-(4-(5-phenylbenzo[b]thiophen-2-yl)phenyl)-4,4,5,5-tetramethyl-1,3,2-dioxaborolane)

To toluene (300 parts), 2-(4-bromophenyl)-5-phenylbenzo[b]thiophene (8.5 parts), which was obtained in the step 23, bis(pinacolato)diboron (6.9 parts), potassium acetate (4.4 parts) and a [1,1'-bis(diphenylphosphino)ferrocene]palladium(II)dichloride dichloromethane adduct (0.64 parts) were mixed, and the mixture was stirred at a reflux temperature for 6 hours, under a nitrogen atmosphere. The obtained reaction liquid was cooled to room temperature. Then, 20 parts of silica gel were added thereto, and the mixture was stirred for 5 minutes. Then, the solid matter was separated by filtration, and the solvent was removed under reduced pressure to obtain 2-(4-(5-phenylbenzo[b]thiophen-2-yl)phenyl)-4,4,5,5-tetramethyl-1,3,2-dioxaborolane (5.2 parts and yield of 55%).

Step 25 (Synthesis of 2,7-bis(4-(5-phenylbenzo[b]thiophen-2-yl)phenyl)[1]benzothieno[3,2-b][1]benzothiophene)

To DMF (200 parts), water (5.0 parts), 2,7-diiodo[1]benzothieno[3,2-b][1]benzothiophene (1.8 parts), which was synthesized according to the method described in Japanese Patent No. 4945757, 2-(4-(5-phenylbenzo[b]thiophen-2-yl)phenyl)-4,4,5,5-tetramethyl-1,3,2-dioxaborolane (4.5 parts), which was obtained in the step 24, tripotassium phosphate (15 parts) and tetrakis(triphenylphosphine)palladium (0.4 parts) were mixed, and the mixture was stirred at 80° C. for 6 hours, under a nitrogen atmosphere. The obtained reaction liquid was cooled to room temperature. Then, water (200 parts) was added thereto, and the solid matter was collected by filtration. The obtained solid matter was washed with acetone, dried, and then purified by sublimation to obtain a compound (1.5 parts and yield of 50%) represented by No. 83 in the specific examples described above.

Synthesis Example 9

Synthesis of 2,7-bis(4-(3-dibenzo[b,d]furan)phenyl)[1]benzothieno[3,2-b][1]benzothiophene (Compound Represented by No. 72 in the Specific Examples)

Step 26 (Synthesis of 2-(3-dibenzo[b,d]furan)-4,4,5,5-tetramethyl-1,3,2-dioxaborolane)

To toluene (100 parts), 3-bromodibenzo[b,d]furan (5.0 parts), bis(pinacolato)diboron (6.2 parts), potassium acetate (4.0 parts) and a [1,1'-bis(diphenylphosphino)ferrocene]palladium(II)dichloride dichloromethane adduct (0.5 parts) were mixed, and the mixture was stirred at a reflux temperature for 5 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene), and the solvent was removed under reduced pressure to obtain 2-(3-dibenzo[b,d]furan)-4,4,5,5-tetramethyl-1,3,2-dioxaborolane (3.8 parts and yield of 64%).

Step 27 (Synthesis of 3-(4-bromophenyl)dibenzo[b,d]furan)

To DMF (60 parts), 2-(3-dibenzo[b,d]furan)-4,4,5,5-tetramethyl-1,3,2-dioxaborolane (3.8 parts), which was obtained in the step 26, 1-bromo-4-iodobenzene (3.7 parts), tripotassium phosphate (5.5 parts) and tetrakis(triphenylphosphine)palladium (0.4 parts) were mixed, and the mixture was stirred at 60° C. for 2 hours, under a nitrogen atmosphere. The obtained reaction liquid was cooled to room temperature. Then, water (200 parts) was added thereto, and the solid matter was collected by filtration. The obtained solid matter was washed with water and methanol in this order to obtain 3-(4-bromophenyl)dibenzo[b,d]furan (2.7 parts and yield of 64%).

Step 28 (Synthesis of 2-(4-(3-dibenzo[b,d]furan)phenyl)-4,4,5,5-tetramethyl-1,3,2-dioxaborolane)

To toluene (50 parts), 3-(4-bromophenyl)dibenzo[b,d]furan (2.7 parts), which was obtained in the step 27, bis(pinacolato)diboron (2.5 parts), potassium acetate (1.6 parts) and a [1,1'-bis(diphenylphosphino)ferrocene]palladium(II)dichloride dichloromethane adduct (0.2 parts), were mixed, and the mixture was stirred at a reflux temperature for 8 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene) to obtain 2-(4-(3-dibenzo[b,d]furan)phenyl)-4,4,5,5-tetramethyl-1,3,2-dioxaborolane (2.8 parts and yield of 90%).

Step 29 (Synthesis of 2,7-bis(4-(3-dibenzo[b,d]furan)phenyl)[1]benzothieno[3,2-b][1]benzothiophene)

To DMF (80 parts), water (8.0 parts), 2,7-diiodo[1]benzothieno[3,2-b][1]benzothiophene (1.5 parts), which was synthesized according to the method described in Japanese Patent No. 4945757, 2-(4-(3-dibenzo[b,d]furan)phenyl)-4,4,5,5-tetramethyl-1,3,2-dioxaborolane (2.8 parts), which was obtained in the step 28, tripotassium phosphate (2.6 parts) and tetrakis(triphenylphosphine)palladium (0.2 parts) were mixed, and the mixture was stirred at 80° C. for 6 hours, under a nitrogen atmosphere. The obtained reaction liquid was cooled to room temperature. Then, water (100 parts) was added thereto, and the solid matter was collected by filtration. The obtained solid matter was washed with acetone and DMF, dried, and then purified by sublimation to obtain a compound (0.9 parts and yield of 41%) represented by No. 72 in the specific examples described above.

Synthesis Example 10

Synthesis of 2,7-bis(4-(3-dibenzo[b,d]thiophene)phenyl)[1]benzothieno[3,2-b][1]benzothiophene (Compound Represented by No. 71 in the Specific Examples)

Step 30 (synthesis of 2-(3-dibenzo[b,d]thiophene)-4,4,5,5-tetramethyl-1,3,2-dioxaborolane)
To toluene (100 parts), 3-bromodibenzo[b,d]thiophene (5.0 parts), bis(pinacolato)diboron (5.8 parts), potassium acetate (3.7 parts) and a [1,1'-bis(diphenylphosphino)ferrocene]palladium(II)dichloride dichloromethane adduct (0.4 parts) were mixed, and the mixture was stirred at a reflux temperature for 4 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene), and the solvent was removed under reduced pressure to obtain 2-(3-dibenzo[b,d]thiophene)-4,4,5,5-tetramethyl-1,3,2-dioxaborolane (2.3 parts and yield of 39%).

Step 31 (Synthesis of 3-(4-bromophenyl)dibenzo[b,d]thiophene)

To DMF (40 parts), 2-(3-dibenzo[b,d]thiophene)-4,4,5,5-tetramethyl-1,3,2-dioxaborolane (2.3 parts), which was obtained in the step 30, 1-bromo-4-iodobenzene (2.1 parts), tripotassium phosphate (3.0 parts) and tetrakis(triphenylphosphine)palladium (0.3 parts) were mixed, and the mixture was stirred at 60° C. for 3 hours, under a nitrogen atmosphere. The obtained reaction liquid was cooled to room temperature. Then, water (60 parts) was added thereto, and the solid matter was collected by filtration. The obtained solid matter was washed with water and methanol in this order to obtain 3-(4-bromophenyl)dibenzo[b,d]thiophene (2.5 parts and yield of 99%).

Step 32 (Synthesis of 2-(4-(3-dibenzo[b,d]thiophene)phenyl)-4,4,5,5-tetramethyl-1,3,2-dioxaborolane)

To toluene (50 parts), 3-(4-bromophenyl)dibenzo[b,d]thiophene (2.5 parts), which was obtained in the step 31, bis(pinacolato)diboron (2.2 parts), potassium acetate (1.4 parts) and a [1,1'-bis(diphenylphosphino)ferrocene]palladium(II)dichloride dichloromethane adduct (0.2 parts) were mixed, and the mixture was stirred at a reflux temperature for 8 hours, under a nitrogen atmosphere. The obtained reaction liquid was cooled to room temperature, and the solid matter was separated by filtration to obtain a filtrate containing the product. Subsequently, the filtrate was purified by short silica gel column chromatography (developing solution: toluene) to obtain 2-(4-(3-dibenzo[b,d]thiophene)phenyl)-4,4,5,5-tetramethyl-1,3,2-dioxaborolane (2.0 parts and yield of 71%).

Step 33 (Synthesis of 2,7-bis(4-(3-dibenzo[b,d]thiophene)phenyl)[1]benzothieno[3,2-b][1]benzothiophene)

To DMF (60 parts), water (8.0 parts), 2,7-diiodo[1]benzothieno[3,2-b][1]benzothiophene (1.0 part), which was synthesized according to the method described in Japanese Patent No. 4945757, 2-(4-(3-dibenzo[b,d]thiophene)phenyl)-4,4,5,5-tetramethyl-1,3,2-dioxaborolane (2.0 parts), which was obtained in the step 32, tripotassium phosphate (1.8 parts) and tetrakis(triphenylphosphine)palladium (0.1 parts) were mixed, and the mixture was stirred at 80° C. for 6 hours, under a nitrogen atmosphere. The obtained reaction liquid was cooled to room temperature. Then, water (100 parts) was added thereto, and the solid matter was collected by filtration. The obtained solid matter was washed with acetone and DMF, dried, and then purified by sublimation to obtain a compound (0.4 parts and yield of 26%) represented by No. 71 in the specific examples described above.

Example 1

Preparation of Photoelectric Conversion Element and Evaluation Thereof

On ITO transparent conductive glass (manufactured by Geomatec Co., Ltd., ITO film thickness: 150 nm), a film of 2,7-bis(4-(benzo[b]thiophen-2-yl)phenyl)[1]benzothieno[3,2-b][1]benzothiophene (compound represented by No. 5 obtained in Synthesis Example 2) was formed as a blocking layer having a thickness of 50 nm by resistance heating vacuum vapor deposition. Next, on the above described blocking layer, a film of quinacridone was formed in vacuum as a photoelectric conversion layer having a thickness of 100 nm. Finally, on the photoelectric conversion layer, a film of aluminum was formed in vacuum as an electrode having a thickness of 100 nm to prepare the photoelectric conversion element for use in an imaging element of the present invention. When a voltage of 5 V was applied with the use of the ITO and aluminum electrodes, the light-dark ratio was $6.7 \times 10^5$.

Example 2

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(benzo[b]furan-2-yl)phenyl)[1]benzothieno[3,2-b][1]benzothiophene (compound represented by No. 1 obtained in Synthesis Example 1) was used, and as a result, the light-dark ratio at the time when a voltage of 5 V was applied was $4.2 \times 10^5$.

Example 3

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(benzo[d]thiazol-2-yl)phenyl)[1]benzothieno[3,2-b][1]benzothiophene (compound represented by No. 29 obtained in Synthesis Example 3) was used, and as a result, the light-dark ratio at the time when a voltage of 5 V was applied was $2.5 \times 10^5$.

Example 4

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(5-benzo[b]thienyl)phenyl)[1]benzothieno[3,2-b][1]benzothiophene (compound obtained in Synthesis Example 4) was used, and as a result, the light-dark ratio at the time when a voltage of 5 V was applied was $5.0 \times 10^5$.

Example 5

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(naphtho[1,2-b]thiophen-2-yl)phenyl)[1]benzothieno[3,2-b][1]benzothiophene (compound represented by No. 69 obtained in Synthesis Example 5) was used, and as a result, the light-dark ratio at the time when a voltage of 5 V was applied was $8.4 \times 10^5$.

Example 6

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(naphtho[2,3-b]thiophen-2-yl)phenyl)[1]benzothieno[3,2-b][1]benzothiophene (compound represented by No. 20 obtained in Synthesis Example 6) was used, and as a result, the light-dark ratio at the time when a voltage of 5 V was applied was $4.5 \times 10^5$.

Example 7

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(benzo[d]oxazol-2-yl)phenyl)[1]benzothieno[3,2-b][1]benzothiophene (compound represented by No. 30 obtained in Synthesis Example 7) was used, and as a result, the light-dark ratio at the time when a voltage of 5 V was applied was $3.5 \times 10^5$.

Example 8

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(4-(5-phenylbenzo[b]thiophen-2-yl)phenyl)[1]benzothieno[3,2-b][1]benzothiophene (compound represented by No. 83 obtained in Synthesis Example 8) was used, and as a result, the light-dark ratio at the time when a voltage of 5 V was applied was $1.0 \times 10^6$.

Example 9

Preparation of Photoelectric Conversion Element and Evaluation Thereof

A photoelectric conversion element was evaluated according to Example 1, except that in place of 2,7-bis(4-

(benzo[b]thiophen-2-yl)phenyl)[1]benzothieno[3,2-b][1]
benzothiophene (compound represented by No. 5 obtained
in Synthesis Example 2), 2,7-bis(4-(3-dibenzo[b,d]furan)
phenyl)[1]benzothieno[3,2-b][1]benzothiophene (compound represented by No. 72 obtained in Synthesis Example
9) was used, and as a result, the light-dark ratio at the time
when a voltage of 5 V was applied was $1.2 \times 10^5$.

Example 10

Preparation of Photoelectric Conversion Element
and Evaluation Thereof

A photoelectric conversion element was evaluated
according to Example 1, except that in place of 2,7-bis(4-(benzo[b]thiophen-2-yl)phenyl)[1]benzothieno[3,2-b][1]
benzothiophene (compound represented by No. 5 obtained
in Synthesis Example 2), 2,7-bis(4-(3-dibenzo[b,d]thiophene)phenyl)[1]benzothieno[3,2-b][1]benzothiophene
(compound represented by No. 71 obtained in Synthesis
Example 10) was used, and as a result, the light-dark ratio
at the time when a voltage of 5 V was applied was $9.2 \times 10^5$.

Comparative Example 1

Preparation of Photoelectric Conversion Element
and Evaluation Thereof

A photoelectric conversion element was evaluated
according to Example 1, except that the 2,7-bis(4-(benzo[b]
thiophen-2-yl)phenyl)[1]benzothieno[3,2-b][1]benzothiophene (compound represented by No. 5 obtained in Synthesis Example 2) was not used, and as a result, the light-dark ratio at the time when a voltage of 5 V was applied was
4.7.

Comparative Example 2

Preparation of Photoelectric Conversion Element
and Evaluation Thereof

A photoelectric conversion element was evaluated
according to Example 1, except that in place of 2,7-bis(4-(benzo[b]thiophen-2-yl)phenyl)[1]benzothieno[3,2-b][1]
benzothiophene (compound represented by No. 5 obtained
in Synthesis Example 2), 2,7-diphenyl[1]benzothieno[3,2-b][1]benzothiophene (compound represented by the following formula (11)) was used, and as a result, the light-dark
ratio at the time when a voltage of 5 V was applied was 600.

(11)

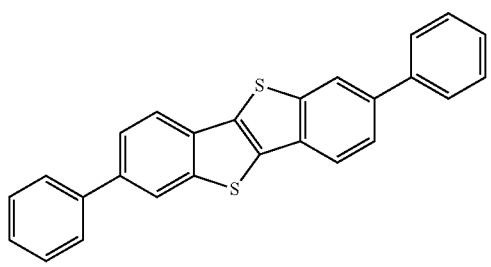

Comparative Example 3

Preparation of Photoelectric Conversion Element
and Evaluation Thereof

A photoelectric conversion element was evaluated
according to Example 1, except that in place of 2,7-bis(4-(benzo[b]thiophen-2-yl)phenyl)[1]benzothieno[3,2-b][1]
benzothiophene (compound represented by No. 5 obtained
in Synthesis Example 2), tris(8-quinolinolato)aluminum was
used, and as a result, the light-dark ratio at the time when a
voltage of 5 V was applied was 31.

Comparative Example 4

Preparation of Photoelectric Conversion Element
and Evaluation Thereof

A photoelectric conversion element was evaluated
according to Example 1, except that in place of 2,7-bis(4-(benzo[b]thiophen-2-yl)phenyl)[1]benzothieno[3,2-b][1]
benzothiophene (compound represented by No. 5 obtained
in Synthesis Example 2), 2,7-bis(9-phenanthrenyl)-[1]benzothieno[3,2-b][1]benzothiophene (compound represented
by the following formula (12)) was used, and as a result, the
light-dark ratio at the time when a voltage of 5 V was applied
was 690.

(12)

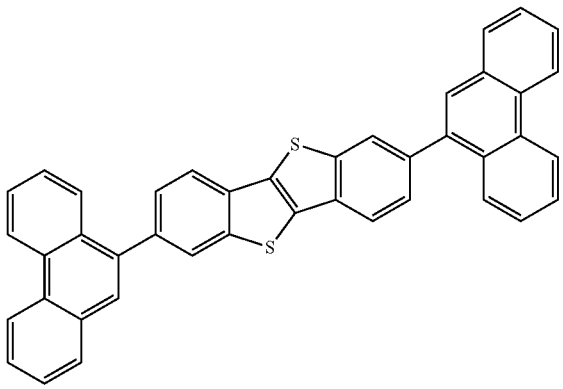

Comparative Example 5

Preparation of Photoelectric Conversion Element
and Evaluation Thereof

A photoelectric conversion element was evaluated
according to Example 1, except that in place of 2,7-bis(4-(benzo[b]thiophen-2-yl)phenyl)[1]benzothieno[3,2-b][1]
benzothiophene (compound represented by No. 5 obtained
in Synthesis Example 2), 2,7-bis(1-naphthyl)-[1]benzothieno[3,2-b][1]benzothiophene (compound represented by
the following formula (13)) was used, and as a result, the
light-dark ratio at the time when a voltage of 5 V was applied
was 240.

(13)

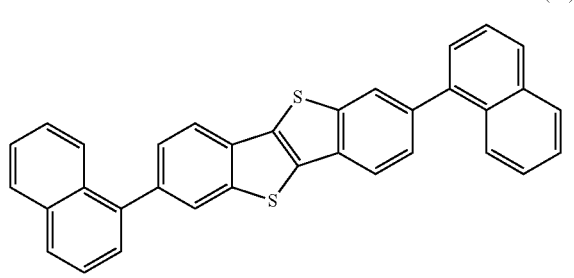

Comparative Example 6

Preparation of Photoelectric Conversion Element and Evaluation Thereof

A photoelectric conversion element was evaluated according to Example 1, except that in place of 2,7-bis(4-(benzo[b]thiophen-2-yl)phenyl)[1]benzothieno[3,2-b][1]benzothiophene (compound represented by No. 5 obtained in Synthesis Example 2), 2,7-bis(9H-carbazol-9-yl)-[1]benzothieno[3,2-b][1]benzothiophene (compound represented by the following formula (14)) was used, and as a result, the light-dark ratio at the time when a voltage of 5 V was applied was 47.

(14)

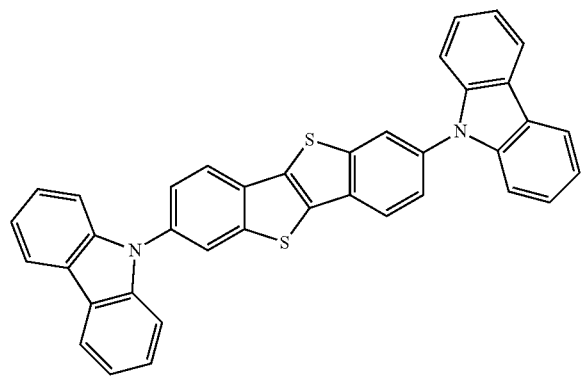

The light-dark ratios obtained in the evaluation of Examples 1 to 9 described above evidently showed excellent characteristics as a photoelectric conversion element for use in an imaging element. In addition, any of the elements had practical transparency to visible light.

It is evident from the above described evaluation results that photoelectric conversion elements for use in imaging elements of the Examples which contain the material for the photoelectric conversion element for use in the imaging element of the present invention, which includes the compound represented by formula (1), have more excellent characteristics than those of the photoelectric conversion elements for use in imaging elements of Comparative Examples.

INDUSTRIAL APPLICABILITY

As described above, the photoelectric conversion element for use in the imaging element containing the material for the photoelectric conversion element for use in the imaging element of the present invention, which includes the compound represented by formula (1), has performance excellent in organic photoelectric conversion characteristics, and is expected to be applied to fields including organic imaging elements having high resolution and high responsiveness as well as organic electronic devices such as organic EL elements, organic solar cell elements and organic transistor elements, as devices such as photo sensors, infrared sensors, ultraviolet sensors, X-ray sensors and photon counters, and as cameras, video cameras, infrared cameras, etc., using these devices.

REFERENCE SIGNS LIST

1 Insulation portion
2 Upper electrode
3 Electron blocking layer or hole transport layer
4 Photoelectric conversion portion
5 Hole blocking layer or electron transport layer
6 Lower electrode
7 Insulating base material or another photoelectric conversion element

The invention claimed is:

1. A material for a photoelectric conversion element for use in an imaging element, comprising a compound represented by the following formula (1):

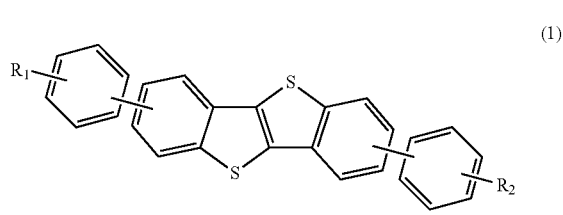

(1)

wherein $R_1$ and $R_2$ independently represent a substituted or unsubstituted benzothienyl group, a substituted or unsubstituted benzofuranyl group, or a substituted or unsubstituted benzothiazole group.

2. The material for a photoelectric conversion element for use in an imaging element according to claim 1, wherein the compound of the formula (1) is a compound represented by the following formula (2):

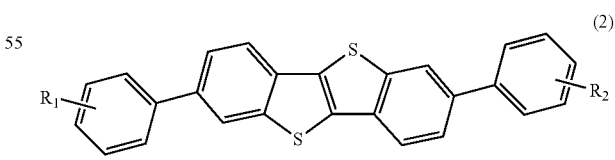

(2)

wherein $R_1$ and $R_2$ are the same as $R_1$ and $R_2$ defined in the formula (1) according to claim 1.

3. The material for a photoelectric conversion element for use in an imaging element according to claim 2, wherein the compound of the formula (2) is a compound represented by the following formula (3):

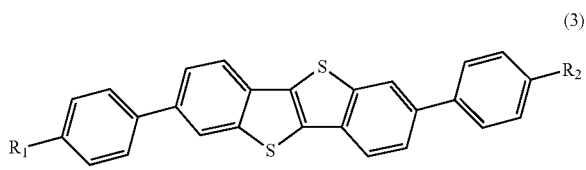
(3)

wherein $R_1$ and $R_2$ are the same as $R_1$ and $R_2$ defined in the formula (1) according to claim 1.

4. The material for a photoelectric conversion element for use in an imaging element according to claim 1, wherein $R_1$ and $R_2$ each represent a substituted or unsubstituted benzo[b]furan group, a substituted or unsubstituted benzo[b]thiophene group, or a substituted or unsubstituted 2-benzo[d]thiazole group.

5. A photoelectric conversion element for use in an imaging element, comprising the material for a photoelectric conversion element for use in an imaging element according to claim 1.

6. A photoelectric conversion element for use in an imaging element, comprising:
a p-type organic semiconductor material; and
an n-type organic semiconductor material,
wherein the p-type organic semiconductor material comprises the material for a photoelectric conversion element for use in an imaging element according to claim 1.

7. A photoelectric conversion element for use in an imaging element, comprising:
a first electrode film (A);
a second electrode film (B); and
a photoelectric conversion portion (C) disposed between the first electrode film and the second electrode film,
wherein the photoelectric conversion portion (C) comprises at least:
a photoelectric conversion layer (c-1); and
an organic thin-film layer (c-2) other than the photoelectric conversion layer, and
wherein the organic thin-film layer (c-2) other than the photoelectric conversion layer comprises the material for a photoelectric conversion element for use in an imaging element according to claim 1.

8. The photoelectric conversion element for use in an imaging element according to claim 7, wherein the organic thin-film layer (c-2) other than the photoelectric conversion layer is an electron blocking layer.

9. The photoelectric conversion element for use in an imaging element according to claim 7, wherein the organic thin-film layer (c-2) other than the photoelectric conversion layer is a hole blocking layer.

10. The photoelectric conversion element for use in an imaging element according to claim 7, wherein the organic thin-film layer (c-2) other than the photoelectric conversion layer is an electron transport layer.

11. The photoelectric conversion element for use in an imaging element according to claim 7, wherein the organic thin-film layer (c-2) other than the photoelectric conversion layer is a hole transport layer.

12. The photoelectric conversion element for use in an imaging element according to claim 5, further comprising:
a thin-film transistor (D) comprising a hole accumulation portion; and
a signal readout portion (E) that reads a signal responding to charge accumulated in the thin-film transistor.

13. The photoelectric conversion element for use in an imaging element according to claim 12, wherein the thin-film transistor (D) comprising a hole accumulation portion further comprises a connection portion (d) electrically connecting the hole accumulation portion to any one of the first electrode film and the second electrode film.

14. An imaging element comprising a plurality of photoelectric conversion elements for use in an imaging element according to claim 7 arranged in an array.

15. A photosensor comprising the photoelectric conversion element for use in an imaging element according to claim 7.

16. A photosensor comprising the imaging element according to claim 14.

\* \* \* \* \*